(12) United States Patent
Shuman et al.

(10) Patent No.: US 6,844,167 B2
(45) Date of Patent: Jan. 18, 2005

(54) PHARMACOLOGICAL TARGETING OF MRNA CAP FORMATION FOR TREATMENT OF PARASITIC INFECTIONS

(76) Inventors: Stewart Shuman, 504 E. 63$^{rd}$ St., Apt. 9R, New York, NY (US) 10021; Chong Kiong Ho, 310 E. 66$^{th}$ St., Apt. 2A, New York, NY (US) 10021

( * ) Notice: Subject to any disclaimer, the term of this patent is extended or adjusted under 35 U.S.C. 154(b) by 268 days.

(21) Appl. No.: 10/167,831

(22) Filed: Jun. 12, 2002

(65) Prior Publication Data

US 2003/0166209 A1 Sep. 4, 2003

Related U.S. Application Data

(62) Division of application No. 09/752,165, filed on Dec. 29, 2000, now Pat. No. 6,451,583.

(51) Int. Cl.$^7$ .............................. C12Q 1/48; C12N 9/12; G01N 33/53
(52) U.S. Cl. .......................... 435/15; 435/194; 435/7.6; 435/7.72
(58) Field of Search .......................... 435/194, 15, 7.6, 435/7.72

(56) References Cited

U.S. PATENT DOCUMENTS

| | | | | |
|---|---|---|---|---|
| 6,107,040 A | * | 8/2000 | Shuman | 435/6 |
| 6,232,070 B1 | * | 5/2001 | Shuman | 435/6 |
| 6,420,163 B1 | * | 7/2002 | Shuman | 435/254.2 |
| 6,451,583 B1 | * | 9/2002 | Shuman et al. | 435/252.3 |

OTHER PUBLICATIONS

Gardner M.J. et al. Genome sequence of the human malaria parasite *Plasmodium falciparum*, Nature, 2002, 419, 498–511.*

* cited by examiner

Primary Examiner—Tekchand Saidha
Assistant Examiner—Malgorzata Walicka
(74) Attorney, Agent, or Firm—Benjamin Aaron Adler

(57) ABSTRACT

This invention provides the genes encoding the RNA triphosphatase and RNA guanylyltransferase of the malaria parasite *Plasmodium falciparum* and the catalytically active recombinant RNA triphosphatase and RNA guanylyltransferase enzymes. These enzymes form the basis of activity inhibition assays to identify molecules that specifically target the formation of the mRNA 5' cap in unicellular eukaryotic parasites.

7 Claims, 13 Drawing Sheets

| | I | | III | | IIIa | | IV | | V | | VI |
|---|---|---|---|---|---|---|---|---|---|---|---|
| Sce (SEQ ID No:3) | KTDGLR | -51- | TLLDGELV | -12- | RYLMFDCLAING | -66- | DGLIF | -15- | LLKWKPEQFNTVD | -105- | WEMLRFRDDK (8) |
| Spo (SEQ ID No:9) | KSDGIR | -48- | TLLDGELV | -11- | RYLVFDCLACDG | -67- | DGLIF | -14- | LLKWKPKEMNTID | -77- | WRFLRFRDDK (14) |
| Cal (SEQ ID No:15) | KTDGLR | -48- | TLLDGELV | -11- | RYVIFDALAIHG | -68- | DGLIY | -14- | LLKWKPAEENTVD | -84- | WEMLRFRNDK (20) |
| ChV (SEQ ID No:21) | KTDGIR | -38- | SIFDGELC | -8- | AFVLFDAVVVSG | -59- | DGLII | -14- | LFKLKPGTHFTID | -44- | WKVIQGRSDK (26) |
| Cel (SEQ ID No:27) | KADGMR | -37- | TLVDTEVI | -14- | RMLIYDIMRFNS | -68- | DGLIF | -14- | VLKWKPPSMNSVD | -61- | WKFMRERTDK (32) |
| Mus (SEQ ID No:33) | KADGTR | -40- | TLLDGEMI | -10- | RYLIYDIIKFNA | -68- | DGLIF | -13- | ILKWKPPSLNSVD | -55- | WVFMRQRIDK (38) |
| Dme (SEQ ID No:39) | KADGTR | -40- | TIVDGEMV | -10- | RYLIYDIVRLSN | -69- | DGLIF | -14- | VFKWKPHELNSVD | -57- | WDFMRERTDK (44) |
| Xla (SEQ ID No:45) | KADGTR | -40- | TLLDGEMI | -10- | RYLIYDIIKENG | -68- | DGLIF | -13- | ILKWKPPNLNSVD | -55- | WVFMRQRVDK (50) |
| Ath1 (SEQ ID No:51) | KADGTR | -43- | TLLDGEMV | -14- | RYLVYDLVAING | -70- | DGLIF | -14- | LLKWK--FVETLD | -58- | WVSLRIRVDK (56) |
| Ath2 (SEQ ID No:57) | KADGTR | -42- | TLLDGEMI | -12- | RYLIYDMVAING | -68- | DGLIF | -14- | LLKWKYPEMNSVD | -65- | WVSMRVRVDK (62) |
| Tbr (SEQ ID No:63) | KADGLR | -55- | FLLDTEVV | -11- | DFIYFWGLDGRR | -50- | DGLVF | -13- | LIKWKPVHLCTVD | -30- | WTFRNARNDK (68) |
| Cfa (SEQ ID No:69) | KVDGQR | -51- | WMLDAELS | -15- | DYVFFGGKQAKR | -55- | DGLIF | -13- | LLKWKPLSLCTAD | -85- | WRLHRLRSDK (74) |
| ASF (SEQ ID No:75) | KADGIR | -30- | TLLDGEFM | -4- | EFYGFDVIMYEG | -62- | DGIIL | -11- | TFKWKPTWDNTLD | -104- | WEIVKIREDR (80) |
| AcNPV (SEQ ID No:81) | KLDGMR | -33- | VAFQCEVM | -19- | NRTQYECGVNAS | -53- | DGYVV | -6- | YVKXKW--MPTTE | -43- | INVLKHRRDR (86) |
| Pfa (SEQ ID No:87) | KTDGVR | -38- | TLLDGELV | -16- | VYLIYDGLYIQR | -218- | DGIIF | -14- | LLKWKPLNLNTVD | -83- | WIAQKIRFDK (92) |

α- ribose 03' ribose O2' guanine base α-phosphate β-phosphate β,γ-phosphates phosphate

Fig. 1

```
MITSTYHPGEKIENEFLKEKIRSKINEMLKWKRRGFPGCNPVSLTNHNIK
NLFTKEYLICEKTDGVRYFLFIASNTTFLIDRNYEIFKNDMHIPTIEDLS
KKQQLTLLDGELVEDILYNEKTGVEEKKIVYLIYDGLYIQRKDITNLSYF
ERLTNVYNYVITPLKKYKKSQKNKKNKNNLQTNHENESLYIELDEKDNIK
KRKSNLNNMLTEEENVLISHKKNDHPHINNKNMNAVNVNGVDVNGVNTNQ
DFNNHNENNNLLMNQCILIDENNNGIQNIGTNDNINSLNNCNLLLYKREE
HREEKEYEEEEDERSYSSDDTASTIHEEEIPFEIYLKDFYPIEKICELIK
IMKKLPHYSDGIIFTPLHSPYITGNFYELLKWKPLNLNTVDFGIETIYDE
YNIPSKFELFISINGVRTSYKCYLAEYGDVYKELLQLAISNKISHYIIEC
YYVSKNIFSICKGENGREQKVEGGWIAQKIRFDKNIPNDISTLNKVIQSI
LDNITIDSLIKEISRNRKAK (SEQ ID No. 1)
```

Fig. 4

```
MVREAHELLDGSRPIPIDKITYELSQNIILAFDNHENINNKDIQIEIEGR
VGLVIDKNKNRIKLPINTDAIIENNYSDFQACIDRESFEYLLDYFHNMTL
KKRLSIRNNDNNNNNMDNNNNNMDNNNNNNNNNIHIHNSGNNTNQTHSYD
KNADDNKPTCNYSYDKKNACIYDFLELKTTKSIDKYYVIKNNNSRIRTTT
YLNDDNKQETESMMIQSLQKDNLNIWNVYTGNNYDYFDDDEEDDDDDYNN
NNNNNNGDTGTKTNIATNNTHGLTTSKSQHIYNNLVDKNDSIDYRISINI
EYTKPISKLYLSKNTPVHERLKERTTFINTYLGLQVDMTKIKTKNNELYE
VEIEIPSKTIFKAMSNLRNKKDSNYLHFICSNLVNNIRGICSQLNVFKKS
KHMLKNTMITKLNNNSNNQNNLSLLPNHPNDDTISSKEKEKFKKYIHSVL
PIVGDYMYRVVTKNEKHIKRKIKDQLITNKEKINIFKNNVDIRRHNKKSL
QTINEVHVENKWKAFKRGTKIEVLLCSDDEEYEQNEDVQDINNEYYDQYK
NEEDTSLYINNIYMHNQINNNNNNNDNDNKNEENLKNYKDFYDDT
```
(SEQ ID No. 2)

Fig. 10

SEQUENCE LISTING

<160> NUMBER OF SEQ ID NOS: 104

<210> SEQ ID NO 1
<211> LENGTH: 520
<212> TYPE: PRT
<213> ORGANISM: Plasmodium falciparum
<220> FEATURE:
<221> NAME/KEY: PEPTIDE
<223> OTHER INFORMATION: Plasmodium falciparum RNA guanylyltransferase Pgt1

<400> SEQUENCE: 1

Met Ile Thr Ser Thr Tyr His Pro Gly Glu Lys Ile Glu Asn Glu
                5                  10                  15
Phe Leu Lys Glu Lys Ile Arg Ser Lys Ile Asn Glu Met Leu Lys
                20                  25                  30
Trp Lys Arg Arg Gly Phe Pro Gly Cys Asn Pro Val Ser Leu Thr
                35                  40                  45
Asn His Asn Ile Lys Asn Leu Phe Thr Lys Glu Tyr Leu Ile Cys
                50                  55                  60
Glu Lys Thr Asp Gly Val Arg Tyr Phe Leu Phe Ile Ala Ser Asn
                65                  70                  75
Thr Thr Phe Leu Ile Asp Arg Asn Tyr Glu Ile Phe Lys Asn Asp
                80                  85                  90
Met His Ile Pro Thr Ile Glu Asp Leu Ser Lys Lys Gln Gln Leu
                95                  100                 105
Thr Leu Leu Asp Gly Glu Leu Val Glu Asp Ile Ile Tyr Asn Glu
                110                 115                 120
Lys Thr Gly Val Glu Glu Lys Lys Ile Val Tyr Leu Ile Tyr Asp
                125                 130                 135
Gly Leu Tyr Ile Gln Arg Lys Asp Ile Thr Asn Leu Ser Tyr Phe
                140                 145                 150
Glu Arg Leu Thr Asn Val Tyr Asn Tyr Val Ile Thr Pro Leu Lys
                155                 160                 165

```
Lys Tyr Lys Lys Ser Gln Lys Asn Lys Asn Lys Asn Leu
            170                 175                 180

Gln Thr Asn His Glu Asn Glu Ser Leu Tyr Ile Glu Leu Asp Glu
            185                 190                 195

Lys Asp Asn Ile Lys Lys Arg Lys Ser Asn Leu Asn Asn Met Leu
            200                 205                 210

Thr Glu Glu Glu Asn Val Leu Ile Ser His Lys Lys Asn Asp His
            215                 220                 225

Pro His Ile Asn Asn Lys Asn Met Asn Ala Val Asn Val Asn Gly
            230                 235                 240

Val Asp Val Asn Gly Val Asn Ile Asn Gln Asp Phe Asn Asn His
            245                 250                 255

Asn Glu Asn Asn Asn Leu Leu Met Asn Gln Gly Ile Leu Ile Asp
            260                 265                 270

Glu Asn Asn Asn Gly Ile Gln Asn Ile Gly Thr Asn Asp Asn Ile
            275                 280                 285

Asn Ser Leu Asn Asn Cys Asn Leu Leu Leu Tyr Lys Arg Glu Glu
            290                 295                 300

His Arg Glu Glu Lys Glu Tyr Glu Glu Glu Asp Glu Arg Ser
            305                 310                 315

Tyr Ser Ser Asp Asp Thr Ala Ser Thr Ile His Glu Glu Glu Ile
            320                 325                 330

Pro Phe Glu Ile Tyr Leu Lys Asp Phe Tyr Pro Ile Glu Lys Ile
            335                 340                 345

Cys Glu Leu Ile Lys Ile Met Lys Lys Leu Pro His Tyr Ser Asp
            350                 355                 360

Gly Ile Ile Phe Thr Pro Leu His Ser Pro Tyr Ile Thr Gly Asn
            365                 370                 375

Phe Tyr Glu Leu Leu Lys Trp Lys Pro Leu Asn Leu Asn Thr Val
            380                 385                 390

Asp Phe Gly Ile Glu Thr Ile Tyr Asp Glu Tyr Asn Ile Pro Ser
            395                 400                 405

Lys Phe Glu Leu Phe Ile Ser Ile Asn Gly Val Arg Thr Ser Tyr
            410                 415                 420

Lys Cys Tyr Leu Ala Glu Tyr Gly Asp Val Tyr Lys Glu Leu Leu
            425                 430                 435

Gln Leu Ala Ile Ser Asn Lys Ile Ser His Tyr Ile Ile Glu Cys
            440                 445                 450

Tyr Tyr Val Ser Lys Asn Ile Phe Ser Ile Cys Lys Gly Glu Asn
            455                 460                 465

Gly Arg Glu Gln Lys Val Glu Gly Gly Trp Ile Ala Gln Lys Ile
            470                 475                 480

Arg Phe Asp Lys Asn Ile Pro Asn Asp Ile Ser Thr Leu Asn Lys
            485                 490                 495

Val Ile Gln Ser Ile Leu Asp Asn Ile Thr Ile Asp Ser Leu Ile
            500                 505                 510

Lys Glu Ile Ser Arg Asn Arg Lys Ala Lys
            515                 520

<210> SEQ ID NO 2
<211> LENGTH: 596
<212> TYPE: PRT
<213> ORGANISM: Plasmodium falciparum
<220> FEATURE:
```

-continued

```
<221> NAME/KEY: PEPTIDE
<223> OTHER INFORMATION: Plasmodium falciparum RNA triphosphatase Prt1

<400> SEQUENCE: 2

Met Val Arg Glu Ala His Glu Leu Leu Asp Gly Ser Arg Pro Ile
                 5                  10                  15

Pro Ile Asp Lys Ile Thr Tyr Glu Leu Ser Gln Asn Ile Ile Leu
                20                  25                  30

Ala Phe Asp Asn His Glu Asn Ile Asn Asn Lys Asp Ile Gln Ile
                35                  40                  45

Glu Ile Glu Gly Arg Val Gly Leu Val Ile Asp Lys Asn Lys Asn
                50                  55                  60

Arg Ile Lys Leu Pro Ile Asn Thr Asp Ala Ile Ile Glu Asn Asn
                65                  70                  75

Tyr Ser Asp Phe Gln Ala Gly Ile Asp Arg Glu Ser Phe Glu Tyr
                80                  85                  90

Leu Leu Asp Tyr Phe His Asn Met Thr Leu Lys Lys Arg Leu Ser
                95                 100                 105

Ile Arg Asn Asn Asp Asn Asn Asn Asn Met Asp Asn Asn Asn
               110                 115                 120

Asn Asn Met Asp Asn Asn Asn Asn Asn Asn Asn Asn Ile His
               125                 130                 135

Ile His Asn Ser Gly Asn Asn Thr Asn Gln Thr His Ser Tyr Asp
               140                 145                 150

Lys Asn Ala Asp Asp Asn Lys Pro Thr Cys Asn Tyr Ser Tyr Asp
               155                 160                 165

Lys Lys Asn Ala Cys Ile Tyr Asp Phe Leu Glu Leu Lys Thr Thr
               170                 175                 180

Lys Ser Ile Asp Lys Tyr Tyr Val Ile Lys Asn Asn Asn Ser Arg
               185                 190                 195

Ile Arg Thr Thr Thr Tyr Leu Asn Asp Asp Asn Lys Gln Glu Thr
               200                 205                 210

Glu Ser Met Met Ile Gln Ser Leu Gln Lys Asp Asn Leu Asn Ile
               215                 220                 225

Trp Asn Val Tyr Thr Gly Asn Asn Tyr Asp Tyr Phe Asp Asp Asp
               230                 235                 240

Glu Glu Asp Asp Asp Asp Asp Tyr Asn Asn Asn Asn Asn Asn Asn
               245                 250                 255

Asn Gly Asp Thr Gly Thr Lys Thr Asn Ile Ala Thr Asn Asn Thr
               260                 265                 270

His Gly Leu Thr Thr Ser Lys Ser Gln His Ile Tyr Asn Asn Leu
               275                 280                 285

Val Asp Lys Asn Asp Ser Ile Asp Tyr Arg Ile Ser Ile Asn Ile
               290                 295                 300

Glu Tyr Thr Lys Pro Ile Ser Lys Leu Tyr Leu Ser Lys Asn Thr
               305                 310                 315

Pro Val His Glu Arg Leu Lys Glu Arg Thr Thr Phe Ile Asn Thr
               320                 325                 330

Tyr Leu Gly Leu Gln Val Asp Met Thr Lys Ile Lys Thr Lys Asn
               335                 340                 345

Asn Glu Leu Tyr Glu Val Glu Ile Glu Ile Pro Ser Lys Thr Ile
               350                 355                 360

Phe Lys Ala Met Ser Asn Leu Arg Asn Lys Lys Asp Ser Asn Tyr
               365                 370                 375
```

-continued

```
Leu His Phe Ile Cys Ser Asn Leu Val Asn Asn Ile Arg Gly Ile
            380                 385                 390

Cys Ser Gln Leu Asn Val Phe Lys Lys Ser Lys His Met Leu Lys
        395                 400                 405

Asn Thr Met Ile Thr Lys Leu Asn Asn Asn Ser Asn Asn Gln Asn
        410                 415                 420

Asn Leu Ser Leu Leu Pro Asn His Pro Asn Asp Asp Thr Ile Ser
        425                 430                 435

Ser Lys Glu Lys Glu Lys Phe Lys Lys Tyr Ile His Ser Val Leu
        440                 445                 450

Pro Ile Val Gly Asp Tyr Met Tyr Arg Val Thr Lys Asn Glu
        455                 460                 465

Lys His Ile Lys Arg Lys Ile Lys Asp Gln Leu Ile Thr Asn Lys
        470                 475                 480

Glu Lys Ile Asn Ile Phe Lys Asn Asn Val Asp Ile Arg Arg His
        485                 490                 495

Asn Lys Lys Ser Leu Gln Thr Ile Asn Glu Val His Val Glu Asn
        500                 505                 510

Lys Trp Lys Ala Phe Lys Arg Gly Thr Lys Ile Glu Val Leu Leu
        515                 520                 525

Cys Ser Asp Asp Glu Glu Tyr Glu Gln Asn Glu Asp Val Gln Asp
        530                 535                 540

Ile Asn Asn Glu Tyr Tyr Asp Gln Tyr Lys Asn Glu Glu Asp Thr
        545                 550                 555

Ser Leu Tyr Ile Asn Asn Ile Tyr Met His Asn Gln Ile Asn Asn
        560                 565                 570

Asn Asn Asn Asn Asn Asp Asn Asp Asn Lys Asn Glu Glu Asn
        575                 580                 585

Leu Lys Asn Tyr Lys Asp Phe Tyr Asp Asp Thr
        590                 595

<210> SEQ ID NO 3
<211> LENGTH: 6
<212> TYPE: PRT
<213> ORGANISM: Saccharomyces cerevisiae
<220> FEATURE:
<221> NAME/KEY: DOMAIN
<223> OTHER INFORMATION: Motif I of RNA guanylyltransferase from
      Saccharomyces cerevisiae

<400> SEQUENCE: 3

Lys Thr Asp Gly Leu Arg
                5

<210> SEQ ID NO 4
<211> LENGTH: 8
<212> TYPE: PRT
<213> ORGANISM: Saccharomyces cerevisiae
<220> FEATURE:
<221> NAME/KEY: DOMAIN
<223> OTHER INFORMATION: Motif III of RNA guanylyltransferase from
      Saccharomyces cerevisiae

<400> SEQUENCE: 4

Thr Leu Leu Asp Gly Glu Leu Val
                5

<210> SEQ ID NO 5
<211> LENGTH: 12
```

```
<212> TYPE: PRT
<213> ORGANISM: Saccharomyces cerevisiae
<220> FEATURE:
<221> NAME/KEY: DOMAIN
<223> OTHER INFORMATION: Motif IIIa of RNA guanylyltransferase from
      Saccharomyces cerevisiae

<400> SEQUENCE: 5

Arg Tyr Leu Met Phe Asp Cys Leu Ala Ile Asn Gly
                5                   10

<210> SEQ ID NO 6
<211> LENGTH: 5
<212> TYPE: PRT
<213> ORGANISM: Saccharomyces cerevisiae
<220> FEATURE:
<221> NAME/KEY: DOMAIN
<223> OTHER INFORMATION: Motif IV of RNA guanylyltransferase from
      Saccharomyces cerevisiae

<400> SEQUENCE: 6

Asp Gly Leu Ile Phe
                5

<210> SEQ ID NO 7
<211> LENGTH: 13
<212> TYPE: PRT
<213> ORGANISM: Saccharomyces cerevisiae
<220> FEATURE:
<221> NAME/KEY: DOMAIN
<223> OTHER INFORMATION: Motif V of RNA guanylyltransferase from
      Saccharomyces cerevisiae

<400> SEQUENCE: 7

Leu Leu Lys Trp Lys Pro Glu Gln Glu Asn Thr Val Asp
                5                   10

<210> SEQ ID NO 8
<211> LENGTH: 10
<212> TYPE: PRT
<213> ORGANISM: Saccharomyces cerevisiae
<220> FEATURE:
<221> NAME/KEY: DOMAIN
<223> OTHER INFORMATION: Motif VI of RNA guanylyltransferase from
      Saccharomyces cerevisiae

<400> SEQUENCE: 8

Trp Glu Met Leu Arg Phe Arg Asp Asp Lys
                5                   10

<210> SEQ ID NO 9
<211> LENGTH: 6
<212> TYPE: PRT
<213> ORGANISM: Schizosaccharomyces pombe
<220> FEATURE:
<221> NAME/KEY: DOMAIN
<223> OTHER INFORMATION: Motif I of RNA guanylyltransferase from
      Schizosaccharomyces pombe

<400> SEQUENCE: 9

Lys Ser Asp Gly Ile Arg
                5

<210> SEQ ID NO 10
<211> LENGTH: 8
<212> TYPE: PRT
<213> ORGANISM: Schizosaccharomyces pombe
<220> FEATURE:
<221> NAME/KEY: DOMAIN
```

<223> OTHER INFORMATION: Motif III of RNA guanylyltransferase from
      Schizosaccharomyces pombe

<400> SEQUENCE: 10

Thr Leu Leu Asp Gly Glu Leu Val
                5

<210> SEQ ID NO 11
<211> LENGTH: 12
<212> TYPE: PRT
<213> ORGANISM: Schizosaccharomyces pombe
<220> FEATURE:
<221> NAME/KEY: DOMAIN
<223> OTHER INFORMATION: Motif IIIa of RNA guanylyltransferase from
      Schizosaccharomyces pombe

<400> SEQUENCE: 11

Arg Tyr Leu Val Phe Asp Cys Leu Ala Cys Asp Gly
                5                  10

<210> SEQ ID NO 12
<211> LENGTH: 5
<212> TYPE: PRT
<213> ORGANISM: Schizosaccharomyces pombe
<220> FEATURE:
<221> NAME/KEY: DOMAIN
<223> OTHER INFORMATION: Motif IV of RNA guanylyltransferase from
      Schizosaccharomyces pombe

<400> SEQUENCE: 12

Asp Gly Leu Ile Phe
                5

<210> SEQ ID NO 13
<211> LENGTH: 13
<212> TYPE: PRT
<213> ORGANISM: Schizosaccharomyces pombe
<220> FEATURE:
<221> NAME/KEY: DOMAIN
<223> OTHER INFORMATION: Motif V of RNA guanylyltransferase from
      Schizosaccharomyces pombe

<400> SEQUENCE: 13

Leu Leu Lys Trp Lys Pro Lys Glu Met Asn Thr Ile Asp
                5                  10

<210> SEQ ID NO 14
<211> LENGTH: 10
<212> TYPE: PRT
<213> ORGANISM: Schizosaccharomyces pombe
<220> FEATURE:
<221> NAME/KEY: DOMAIN
<223> OTHER INFORMATION: Motif VI of RNA guanylyltransferase from
      Schizosaccharomyces pombe

<400> SEQUENCE: 14

Trp Arg Phe Leu Arg Phe Arg Asp Asp Lys
                5                  10

<210> SEQ ID NO 15
<211> LENGTH: 6
<212> TYPE: PRT
<213> ORGANISM: Candida albicans
<220> FEATURE:
<221> NAME/KEY: DOMAIN
<223> OTHER INFORMATION: Motif I of RNA guanylyltransferase from C.
      albicans

<400> SEQUENCE: 15

-continued

```
Lys Thr Asp Gly Leu Arg
                5

<210> SEQ ID NO 16
<211> LENGTH: 8
<212> TYPE: PRT
<213> ORGANISM: Candida albicans
<220> FEATURE:
<221> NAME/KEY: DOMAIN
<223> OTHER INFORMATION: Motif III of RNA guanylyltransferase from
      C. albicans

<400> SEQUENCE: 16

Thr Leu Leu Asp Gly Glu Leu Val
                5

<210> SEQ ID NO 17
<211> LENGTH: 12
<212> TYPE: PRT
<213> ORGANISM: Candida albicans
<220> FEATURE:
<221> NAME/KEY: DOMAIN
<223> OTHER INFORMATION: Motif IIIa of RNA guanylyltransferase from
      C. albicans

<400> SEQUENCE: 17

Arg Tyr Val Ile Phe Asp Ala Leu Ala Ile His Gly
                5                   10

<210> SEQ ID NO 18
<211> LENGTH: 5
<212> TYPE: PRT
<213> ORGANISM: Candida albicans
<220> FEATURE:
<221> NAME/KEY: DOMAIN
<223> OTHER INFORMATION: Motif IV of RNA guanylyltransferase from
      C. albicans

<400> SEQUENCE: 18

Asp Gly Leu Ile Tyr
                5

<210> SEQ ID NO 19
<211> LENGTH: 13
<212> TYPE: PRT
<213> ORGANISM: Candida albicans
<220> FEATURE:
<221> NAME/KEY: DOMAIN
<223> OTHER INFORMATION: Motif V of RNA guanylyltransferase from C.
      albicans

<400> SEQUENCE: 19

Leu Leu Lys Trp Lys Pro Ala Glu Glu Asn Thr Val Asp
                5                   10

<210> SEQ ID NO 20
<211> LENGTH: 10
<212> TYPE: PRT
<213> ORGANISM: Candida albicans
<220> FEATURE:
<221> NAME/KEY: DOMAIN
<223> OTHER INFORMATION: Motif VI of RNA guanylyltransferase from
      C. albicans

<400> SEQUENCE: 20

Trp Glu Met Leu Arg Phe Arg Asn Asp Lys
                5                   10
```

```
<210> SEQ ID NO 21
<211> LENGTH: 6
<212> TYPE: PRT
<213> ORGANISM: Chlorella
<220> FEATURE:
<221> NAME/KEY: DOMAIN
<223> OTHER INFORMATION: Motif I of RNA guanylyltransferase from
      Chlorella virus PBCV-1

<400> SEQUENCE: 21

Lys Thr Asp Gly Ile Arg
                5

<210> SEQ ID NO 22
<211> LENGTH: 8
<212> TYPE: PRT
<213> ORGANISM: Chlorella
<220> FEATURE:
<221> NAME/KEY: DOMAIN
<223> OTHER INFORMATION: Motif III of RNA guanylyltransferase from
      Chlorella virus PBCV-1

<400> SEQUENCE: 22

Ser Ile Phe Asp Gly Glu Leu Cys
                5

<210> SEQ ID NO 23
<211> LENGTH: 12
<212> TYPE: PRT
<213> ORGANISM: Chlorella
<220> FEATURE:
<221> NAME/KEY: DOMAIN
<223> OTHER INFORMATION: Motif IIIa of RNA guanylyltransferase
      from Chlorella virus PBCV-1

<400> SEQUENCE: 23

Ala Phe Val Leu Phe Asp Ala Val Val Val Ser Gly
                5                  10

<210> SEQ ID NO 24
<211> LENGTH: 5
<212> TYPE: PRT
<213> ORGANISM: Chlorella
<220> FEATURE:
<221> NAME/KEY: DOMAIN
<223> OTHER INFORMATION: Motif IV of RNA guanylyltransferase from
      Chlorella virus PBCV-1

<400> SEQUENCE: 24

Asp Gly Leu Ile Ile
                5

<210> SEQ ID NO 25
<211> LENGTH: 13
<212> TYPE: PRT
<213> ORGANISM: Chlorella
<220> FEATURE:
<221> NAME/KEY: DOMAIN
<223> OTHER INFORMATION: Motif V of RNA guanylyltransferase from
      Chlorella virus PBCV-1

<400> SEQUENCE: 25

Leu Phe Lys Leu Lys Pro Gly Thr His His Thr Ile Asp
                5                  10

<210> SEQ ID NO 26
<211> LENGTH: 10
<212> TYPE: PRT
```

```
<213> ORGANISM: Chlorella
<220> FEATURE:
<221> NAME/KEY: DOMAIN
<223> OTHER INFORMATION: Motif VI of RNA guanylyltransferase from
      Chlorella virus PBCV-1

<400> SEQUENCE: 26

Trp Lys Tyr Ile Gln Gly Arg Ser Asp Lys
                5                   10

<210> SEQ ID NO 27
<211> LENGTH: 6
<212> TYPE: PRT
<213> ORGANISM: Caenorhabditis elegans
<220> FEATURE:
<221> NAME/KEY: DOMAIN
<223> OTHER INFORMATION: Motif I of RNA guanylyltransferase from
      Caenorhabditis elegans

<400> SEQUENCE: 27

Lys Ala Asp Gly Met Arg
                5

<210> SEQ ID NO 28
<211> LENGTH: 8
<212> TYPE: PRT
<213> ORGANISM: Caenorhabditis elegans
<220> FEATURE:
<221> NAME/KEY: DOMAIN
<223> OTHER INFORMATION: Motif III of RNA guanylyltransferase from
      Caenorhabditis elegans

<400> SEQUENCE: 28

Thr Leu Val Asp Thr Glu Val Ile
                5

<210> SEQ ID NO 29
<211> LENGTH: 12
<212> TYPE: PRT
<213> ORGANISM: Caenorhabditis elegans
<220> FEATURE:
<221> NAME/KEY: DOMAIN
<223> OTHER INFORMATION: Motif IIIa of RNA guanylyltransferase from
      Caenorhabditis elegans

<400> SEQUENCE: 29

Arg Met Leu Ile Tyr Asp Ile Met Arg Phe Asn Ser
                5                   10

<210> SEQ ID NO 30
<211> LENGTH: 5
<212> TYPE: PRT
<213> ORGANISM: Caenorhabditis elegans
<220> FEATURE:
<221> NAME/KEY: DOMAIN
<223> OTHER INFORMATION: Motif IV of RNA guanylyltransferase from
      Caenorhabditis elegans

<400> SEQUENCE: 30

Asp Gly Leu Ile Phe
                5

<210> SEQ ID NO 31
<211> LENGTH: 13
<212> TYPE: PRT
<213> ORGANISM: Caenorhabditis elegans
<220> FEATURE:
<221> NAME/KEY: DOMAIN
<223> OTHER INFORMATION: Motif V of RNA guanylyltransferase from
```

-continued

```
                Caenorhabditis elegans

<400> SEQUENCE: 31

Val Leu Lys Trp Lys Pro Pro Ser His Asn Ser Val Asp
                5                   10

<210> SEQ ID NO 32
<211> LENGTH: 10
<212> TYPE: PRT
<213> ORGANISM: Caenorhabditis elegans
<220> FEATURE:
<221> NAME/KEY: DOMAIN
<223> OTHER INFORMATION: Motif VI of RNA guanylyltransferase from
      Caenorhabditis elegans

<400> SEQUENCE: 32

Trp Lys Phe Met Arg Glu Arg Thr Asp Lys
                5                   10

<210> SEQ ID NO 33
<211> LENGTH: 6
<212> TYPE: PRT
<213> ORGANISM: Unknown
<220> FEATURE:
<221> NAME/KEY: DOMAIN
<223> OTHER INFORMATION: Motif I of RNA guanylyltransferase from mouse

<400> SEQUENCE: 33

Lys Ala Asp Gly Thr Arg
                5

<210> SEQ ID NO 34
<211> LENGTH: 8
<212> TYPE: PRT
<213> ORGANISM: Unknown
<220> FEATURE:
<221> NAME/KEY: DOMAIN
<223> OTHER INFORMATION: Motif III of RNA guanylyltransferase from mouse

<400> SEQUENCE: 34

Thr Leu Leu Asp Gly Glu Met Ile
                5

<210> SEQ ID NO 35
<211> LENGTH: 12
<212> TYPE: PRT
<213> ORGANISM: Unknown
<220> FEATURE:
<221> NAME/KEY: DOMAIN
<223> OTHER INFORMATION: Motif IIIa of RNA guanylyltransferase from
      mouse

<400> SEQUENCE: 35

Arg Tyr Leu Ile Tyr Asp Ile Ile Lys Phe Asn Ala
                5                   10

<210> SEQ ID NO 36
<211> LENGTH: 5
<212> TYPE: PRT
<213> ORGANISM: Unknown
<220> FEATURE:
<221> NAME/KEY: DOMAIN
<223> OTHER INFORMATION: Motif IV of RNA guanylyltransferase from mouse

<400> SEQUENCE: 36

Asp Gly Leu Ile Phe
                5
```

-continued

```
<210> SEQ ID NO 37
<211> LENGTH: 13
<212> TYPE: PRT
<213> ORGANISM: Unknown
<220> FEATURE:
<221> NAME/KEY: DOMAIN
<223> OTHER INFORMATION: Motif V of RNA guanylyltransferase from mouse

<400> SEQUENCE: 37

Ile Leu Lys Trp Lys Pro Pro Ser Leu Asn Ser Val Asp
                5                   10

<210> SEQ ID NO 38
<211> LENGTH: 10
<212> TYPE: PRT
<213> ORGANISM: Unknown
<220> FEATURE:
<221> NAME/KEY: DOMAIN
<223> OTHER INFORMATION: Motif VI of RNA guanylyltransferase from mouse

<400> SEQUENCE: 38

Trp Val Phe Met Arg Gln Arg Ile Asp Lys
                5                   10

<210> SEQ ID NO 39
<211> LENGTH: 6
<212> TYPE: PRT
<213> ORGANISM: Drosophila melanogaster
<220> FEATURE:
<221> NAME/KEY: DOMAIN
<223> OTHER INFORMATION: Motif I of RNA guanylyltransferase from
      Drosophila melanogaster

<400> SEQUENCE: 39

Lys Ala Asp Gly Thr Arg
                5

<210> SEQ ID NO 40
<211> LENGTH: 8
<212> TYPE: PRT
<213> ORGANISM: Drosophila melanogaster
<220> FEATURE:
<221> NAME/KEY: DOMAIN
<223> OTHER INFORMATION: Motif III of RNA guanylyltransferase from
      Drosophila melanogaster

<400> SEQUENCE: 40

Thr Leu Val Asp Gly Glu Met Val
                5

<210> SEQ ID NO 41
<211> LENGTH: 12
<212> TYPE: PRT
<213> ORGANISM: Drosophila melanogaster
<220> FEATURE:
<221> NAME/KEY: DOMAIN
<223> OTHER INFORMATION: Motif IIIa of RNA guanylyltransferase from
      Drosophila melanogaster

<400> SEQUENCE: 41

Arg Tyr Leu Ile Tyr Asp Ile Val Arg Leu Ser Asn
                5                   10

<210> SEQ ID NO 42
<211> LENGTH: 5
<212> TYPE: PRT
<213> ORGANISM: Drosophila melanogaster
<220> FEATURE:
```

-continued

```
<221> NAME/KEY: DOMAIN
<223> OTHER INFORMATION: Motif IV of RNA guanylyltransferase from
      Drosophila melanogaster

<400> SEQUENCE: 42

Asp Gly Leu Ile Phe
              5

<210> SEQ ID NO 43
<211> LENGTH: 13
<212> TYPE: PRT
<213> ORGANISM: Drosophila melanogaster
<220> FEATURE:
<221> NAME/KEY: DOMAIN
<223> OTHER INFORMATION: Motif V of RNA guanylyltransferase from
      Drosophila melanogaster

<400> SEQUENCE: 43

Val Phe Lys Trp Lys Pro His Glu Leu Asn Ser Val Asp
              5                  10

<210> SEQ ID NO 44
<211> LENGTH: 10
<212> TYPE: PRT
<213> ORGANISM: Drosophila melanogaster
<220> FEATURE:
<221> NAME/KEY: DOMAIN
<223> OTHER INFORMATION: Motif VI of RNA guanylyltransferase from
      Drosophila melanogaster

<400> SEQUENCE: 44

Trp Asp Phe Met Arg Glu Arg Thr Asp Lys
              5                  10

<210> SEQ ID NO 45
<211> LENGTH: 6
<212> TYPE: PRT
<213> ORGANISM: Xenopus laevis
<220> FEATURE:
<221> NAME/KEY: DOMAIN
<223> OTHER INFORMATION: Motif I of RNA guanylyltransferase from
      Xenopus laevis

<400> SEQUENCE: 45

Lys Ala Asp Gly Thr Arg
              5

<210> SEQ ID NO 46
<211> LENGTH: 8
<212> TYPE: PRT
<213> ORGANISM: Xenopus laevis
<220> FEATURE:
<221> NAME/KEY: DOMAIN
<223> OTHER INFORMATION: Motif III of RNA guanylyltransferase from
      Xenopus laevis

<400> SEQUENCE: 46

Thr Leu Leu Asp Gly Glu Met Ile
              5

<210> SEQ ID NO 47
<211> LENGTH: 12
<212> TYPE: PRT
<213> ORGANISM: Xenopus laevis
<220> FEATURE:
<221> NAME/KEY: DOMAIN
<223> OTHER INFORMATION: Motif IIIa of RNA guanylyltransferase from
      Xenopus laevis
```

```
<400> SEQUENCE: 47

Arg Tyr Leu Ile Tyr Asp Ile Ile Lys Phe Asn Gly
                5                  10

<210> SEQ ID NO 48
<211> LENGTH: 5
<212> TYPE: PRT
<213> ORGANISM: Xenopus laevis
<220> FEATURE:
<221> NAME/KEY: DOMAIN
<223> OTHER INFORMATION: Motif IV of RNA guanylyltransferase from
      Xenopus laevis

<400> SEQUENCE: 48

Asp Gly Leu Ile Phe
                5

<210> SEQ ID NO 49
<211> LENGTH: 13
<212> TYPE: PRT
<213> ORGANISM: Xenopus laevis
<220> FEATURE:
<221> NAME/KEY: DOMAIN
<223> OTHER INFORMATION: Motif V of RNA guanylyltransferase from
      Xenopus laevis

<400> SEQUENCE: 49

Ile Leu Lys Trp Lys Pro Pro Asn Leu Asn Ser Val Asp
                5                  10

<210> SEQ ID NO 50
<211> LENGTH: 10
<212> TYPE: PRT
<213> ORGANISM: Xenopus laevis
<220> FEATURE:
<221> NAME/KEY: DOMAIN
<223> OTHER INFORMATION: Motif VI of RNA guanylyltransferase from
      Xenopus laevis

<400> SEQUENCE: 50

Trp Val Phe Met Arg Gln Arg Val Asp Lys
                5                  10

<210> SEQ ID NO 51
<211> LENGTH: 6
<212> TYPE: PRT
<213> ORGANISM: Arabidopsis thaliana
<220> FEATURE:
<221> NAME/KEY: DOMAIN
<223> OTHER INFORMATION: Motif I of RNA guanylyltransferase from
      Arabidopsis thaliana

<400> SEQUENCE: 51

Lys Ala Asp Gly Thr Arg
                5

<210> SEQ ID NO 52
<211> LENGTH: 8
<212> TYPE: PRT
<213> ORGANISM: Arabidopsis thaliana
<220> FEATURE:
<221> NAME/KEY: DOMAIN
<223> OTHER INFORMATION: Motif III of RNA guanylyltransferase from
      Arabidopsis thaliana

<400> SEQUENCE: 52

Thr Leu Leu Asp Gly Glu Met Val
                5
```

<210> SEQ ID NO 53
<211> LENGTH: 12
<212> TYPE: PRT
<213> ORGANISM: Arabidopsis thaliana
<220> FEATURE:
<221> NAME/KEY: DOMAIN
<223> OTHER INFORMATION: Motif IIIa of RNA guanylyltransferase from
      Arabidopsis thaliana

<400> SEQUENCE: 53

Arg Tyr Leu Val Tyr Asp Leu Val Ala Ile Asn Gly
                 5                  10

<210> SEQ ID NO 54
<211> LENGTH: 5
<212> TYPE: PRT
<213> ORGANISM: Arabidopsis thaliana
<220> FEATURE:
<221> NAME/KEY: DOMAIN
<223> OTHER INFORMATION: Motif IV of RNA guanylyltransferase from
      Arabidopsis thaliana

<400> SEQUENCE: 54

Asp Gly Leu Ile Phe
                 5

<210> SEQ ID NO 55
<211> LENGTH: 11
<212> TYPE: PRT
<213> ORGANISM: Arabidopsis thaliana
<220> FEATURE:
<221> NAME/KEY: DOMAIN
<223> OTHER INFORMATION: Motif V of RNA guanylyltransferase from
      Arabidopsis thaliana

<400> SEQUENCE: 55

Leu Leu Lys Trp Lys Phe Val Glu Thr Leu Asp
                 5                  10

<210> SEQ ID NO 56
<211> LENGTH: 10
<212> TYPE: PRT
<213> ORGANISM: Arabidopsis thaliana
<220> FEATURE:
<221> NAME/KEY: DOMAIN
<223> OTHER INFORMATION: Motif VI of RNA guanylyltransferase from
      Arabidopsis thaliana

<400> SEQUENCE: 56

Trp Val Ser Leu Arg Ile Arg Val Asp Lys
                 5                  10

<210> SEQ ID NO 57
<211> LENGTH: 6
<212> TYPE: PRT
<213> ORGANISM: Arabidopsis thaliana
<220> FEATURE:
<221> NAME/KEY: DOMAIN
<223> OTHER INFORMATION: Motif I of RNA guanylyltransferase from
      Arabidopsis thaliana

<400> SEQUENCE: 57

Lys Ala Asp Gly Thr Arg
                 5

<210> SEQ ID NO 58
<211> LENGTH: 8

```
<212> TYPE: PRT
<213> ORGANISM: Arabidopsis thaliana
<220> FEATURE:
<221> NAME/KEY: DOMAIN
<223> OTHER INFORMATION: Motif III of RNA guanylyltransferase from
      Arabidopsis thaliana

<400> SEQUENCE: 58

Thr Leu Leu Asp Gly Glu Met Ile
                5

<210> SEQ ID NO 59
<211> LENGTH: 12
<212> TYPE: PRT
<213> ORGANISM: Arabidopsis thaliana
<220> FEATURE:
<221> NAME/KEY: DOMAIN
<223> OTHER INFORMATION: Motif IIIa of RNA guanylyltransferase from
      Arabidopsis thaliana

<400> SEQUENCE: 59

Arg Tyr Leu Ile Tyr Asp Met Val Ala Ile Asn Gly
                5                   10

<210> SEQ ID NO 60
<211> LENGTH: 5
<212> TYPE: PRT
<213> ORGANISM: Arabidopsis thaliana
<220> FEATURE:
<221> NAME/KEY: DOMAIN
<223> OTHER INFORMATION: Motif IV of RNA guanylyltransferase from
      Arabidopsis thaliana

<400> SEQUENCE: 60

Asp Gly Leu Ile Phe
                5

<210> SEQ ID NO 61
<211> LENGTH: 13
<212> TYPE: PRT
<213> ORGANISM: Arabidopsis thaliana
<220> FEATURE:
<221> NAME/KEY: DOMAIN
<223> OTHER INFORMATION: Motif V of RNA guanylyltransferase from
      Arabidopsis thaliana

<400> SEQUENCE: 61

Leu Leu Lys Trp Lys Tyr Pro Glu Met Asn Ser Val Asp
                5                   10

<210> SEQ ID NO 62
<211> LENGTH: 10
<212> TYPE: PRT
<213> ORGANISM: Arabidopsis thaliana
<220> FEATURE:
<221> NAME/KEY: DOMAIN
<223> OTHER INFORMATION: Motif VI of RNA guanylyltransferase from
      Arabidopsis thaliana

<400> SEQUENCE: 62

Trp Val Ser Met Arg Val Arg Val Asp Lys
                5                   10

<210> SEQ ID NO 63
<211> LENGTH: 6
<212> TYPE: PRT
<213> ORGANISM: Trypanosoma brucei gambiense
<220> FEATURE:
<221> NAME/KEY: DOMAIN
```

```
<223> OTHER INFORMATION: Motif I of RNA guanylyltransferase from
      Trypanosoma brucei gambiense

<400> SEQUENCE: 63

Lys Ala Asp Gly Leu Arg
                  5

<210> SEQ ID NO 64
<211> LENGTH: 8
<212> TYPE: PRT
<213> ORGANISM: Trypanosoma brucei gambiense
<220> FEATURE:
<221> NAME/KEY: DOMAIN
<223> OTHER INFORMATION: Motif III of RNA guanylyltransferase from
      Trypanosoma brucei gambiense

<400> SEQUENCE: 64

Phe Leu Leu Asp Thr Glu Val Val
                  5

<210> SEQ ID NO 65
<211> LENGTH: 12
<212> TYPE: PRT
<213> ORGANISM: Trypanosoma brucei gambiense
<220> FEATURE:
<221> NAME/KEY: DOMAIN
<223> OTHER INFORMATION: Motif IIIa of RNA guanylyltransferase from
      Trypanosoma brucei gambiense

<400> SEQUENCE: 65

Asp Phe Ile Tyr Phe Trp Gly Leu Asp Gly Arg Arg
                  5                  10

<210> SEQ ID NO 66
<211> LENGTH: 5
<212> TYPE: PRT
<213> ORGANISM: Trypanosoma brucei gambiense
<220> FEATURE:
<221> NAME/KEY: DOMAIN
<223> OTHER INFORMATION: Motif IV of RNA guanylyltransferase from
      Trypanosoma brucei gambiense

<400> SEQUENCE: 66

Asp Gly Leu Ile Phe
                  5

<210> SEQ ID NO 67
<211> LENGTH: 13
<212> TYPE: PRT
<213> ORGANISM: Trypanosoma brucei gambiense
<220> FEATURE:
<221> NAME/KEY: DOMAIN
<223> OTHER INFORMATION: Motif V of RNA guanylyltransferase from
      Trypanosoma brucei gambiense

<400> SEQUENCE: 67

Leu Ile Lys Trp Lys Pro Val His Leu Cys Thr Val Asp
                  5                  10

<210> SEQ ID NO 68
<211> LENGTH: 10
<212> TYPE: PRT
<213> ORGANISM: Trypanosoma brucei gambiense
<220> FEATURE:
<221> NAME/KEY: DOMAIN
<223> OTHER INFORMATION: Motif VI of RNA guanylyltransferase from
      Trypanosoma brucei gambiense

<400> SEQUENCE: 68
```

Trp Thr Phe Arg Asn Ala Arg Asn Asp Lys
                5                   10

<210> SEQ ID NO 69
<211> LENGTH: 6
<212> TYPE: PRT
<213> ORGANISM: Crithidia fasciculata
<220> FEATURE:
<221> NAME/KEY: DOMAIN
<223> OTHER INFORMATION: Motif I of RNA guanylyltransferase from
      Crithidia fasciculata

<400> SEQUENCE: 69

Lys Val Asp Gly Gln Arg
                5

<210> SEQ ID NO 70
<211> LENGTH: 8
<212> TYPE: PRT
<213> ORGANISM: Crithidia fasciculata
<220> FEATURE:
<221> NAME/KEY: DOMAIN
<223> OTHER INFORMATION: Motif III of RNA guanylyltransferase from
      Crithidia fasciculata

<400> SEQUENCE: 70

Trp Met Leu Asp Ala Glu Leu Ser
                5

<210> SEQ ID NO 71
<211> LENGTH: 12
<212> TYPE: PRT
<213> ORGANISM: Crithidia fasciculata
<220> FEATURE:
<221> NAME/KEY: DOMAIN
<223> OTHER INFORMATION: Motif IIIa of RNA guanylyltransferase from
      Crithidia fasciculata

<400> SEQUENCE: 71

Asp Tyr Val Phe Phe Gly Gly Lys Gln Ala Lys Arg
                5                   10

<210> SEQ ID NO 72
<211> LENGTH: 5
<212> TYPE: PRT
<213> ORGANISM: Crithidia fasciculata
<220> FEATURE:
<221> NAME/KEY: DOMAIN
<223> OTHER INFORMATION: Motif IV of RNA guanylyltransferase from
      Crithidia fasciculata

<400> SEQUENCE: 72

Asp Gly Leu Val Phe
                5

<210> SEQ ID NO 73
<211> LENGTH: 13
<212> TYPE: PRT
<213> ORGANISM: Crithidia fasciculata
<220> FEATURE:
<221> NAME/KEY: DOMAIN
<223> OTHER INFORMATION: Motif V of RNA guanylyltransferase from
      Crithidia fasciculata

<400> SEQUENCE: 73

Leu Leu Lys Trp Lys Pro Leu Ser Leu Cys Thr Ala Asp
                5                   10

```
<210> SEQ ID NO 74
<211> LENGTH: 10
<212> TYPE: PRT
<213> ORGANISM: Crithidia fasciculata
<220> FEATURE:
<221> NAME/KEY: DOMAIN
<223> OTHER INFORMATION: Motif VI of RNA guanylyltransferase from
      Crithidia fasciculata

<400> SEQUENCE: 74

Trp Arg Leu His Arg Leu Arg Ser Asp Lys
                 5                  10

<210> SEQ ID NO 75
<211> LENGTH: 6
<212> TYPE: PRT
<213> ORGANISM: Unknown
<220> FEATURE:
<221> NAME/KEY: DOMAIN
<223> OTHER INFORMATION: Motif I of RNA guanylyltransferase from
      African swine fever virus

<400> SEQUENCE: 75

Lys Ala Asp Gly Ile Arg
                 5

<210> SEQ ID NO 76
<211> LENGTH: 8
<212> TYPE: PRT
<213> ORGANISM: Unknown
<220> FEATURE:
<221> NAME/KEY: DOMAIN
<223> OTHER INFORMATION: Motif III of RNA guanylyltransferase from
      African swine fever virus

<400> SEQUENCE: 76

Thr Ile Leu Asp Gly Glu Phe Met
                 5

<210> SEQ ID NO 77
<211> LENGTH: 12
<212> TYPE: PRT
<213> ORGANISM: Unknown
<220> FEATURE:
<221> NAME/KEY: DOMAIN
<223> OTHER INFORMATION: Motif IIIa of RNA guanylyltransferase from
      African swine fever virus

<400> SEQUENCE: 77

Glu Phe Tyr Gly Phe Asp Val Ile Met Tyr Glu Gly
                 5                  10

<210> SEQ ID NO 78
<211> LENGTH: 5
<212> TYPE: PRT
<213> ORGANISM: Unknown
<220> FEATURE:
<221> NAME/KEY: DOMAIN
<223> OTHER INFORMATION: Motif IV of RNA guanylyltransferase from
      African swine fever virus

<400> SEQUENCE: 78

Asp Gly Ile Ile Leu
                 5

<210> SEQ ID NO 79
<211> LENGTH: 13
<212> TYPE: PRT
```

```
<213> ORGANISM: Unknown
<220> FEATURE:
<221> NAME/KEY: DOMAIN
<223> OTHER INFORMATION: Motif V of RNA guanylyltransferase from
      African swine fever virus

<400> SEQUENCE: 79

Thr Phe Lys Trp Lys Pro Thr Trp Asp Asn Thr Leu Asp
                5                   10

<210> SEQ ID NO 80
<211> LENGTH: 10
<212> TYPE: PRT
<213> ORGANISM: Unknown
<220> FEATURE:
<221> NAME/KEY: DOMAIN
<223> OTHER INFORMATION: Motif VI of RNA guanylyltransferase from
      African swine fever virus

<400> SEQUENCE: 80

Trp Glu Ile Val Lys Ile Arg Glu Asp Arg
                5                   10

<210> SEQ ID NO 81
<211> LENGTH: 6
<212> TYPE: PRT
<213> ORGANISM: Unknown
<220> FEATURE:
<221> NAME/KEY: DOMAIN
<223> OTHER INFORMATION: Motif I of RNA guanylyltransferase from
      AcNPV baculovirus

<400> SEQUENCE: 81

Lys Leu Asp Gly Met Arg
                5

<210> SEQ ID NO 82
<211> LENGTH: 8
<212> TYPE: PRT
<213> ORGANISM: Unknown
<220> FEATURE:
<221> NAME/KEY: DOMAIN
<223> OTHER INFORMATION: Motif III of RNA guanylyltransferase from
      AcNPV baculovirus

<400> SEQUENCE: 82

Val Ala Phe Gln Cys Glu Val Met
                5

<210> SEQ ID NO 83
<211> LENGTH: 12
<212> TYPE: PRT
<213> ORGANISM: Unknown
<220> FEATURE:
<221> NAME/KEY: DOMAIN
<223> OTHER INFORMATION: Motif IIIa of RNA guanylyltransferase from
      AcNPV baculovirus

<400> SEQUENCE: 83

Asn Arg Thr Gln Tyr Glu Cys Gly Val Asn Ala Ser
                5                   10

<210> SEQ ID NO 84
<211> LENGTH: 5
<212> TYPE: PRT
<213> ORGANISM: Unknown
<220> FEATURE:
<221> NAME/KEY: DOMAIN
<223> OTHER INFORMATION: Motif IV of RNA guanylyltransferase from
```

AcNPV baculovirus

<400> SEQUENCE: 84

Asp Gly Tyr Val Val
                5

<210> SEQ ID NO 85
<211> LENGTH: 11
<212> TYPE: PRT
<213> ORGANISM: Unknown
<220> FEATURE:
<221> NAME/KEY: DOMAIN
<223> OTHER INFORMATION: Motif V of RNA guanylyltransferase from
      AcNPV baculovirus

<400> SEQUENCE: 85

Tyr Val Lys Tyr Lys Trp Met Pro Thr Thr Glu
                5                  10

<210> SEQ ID NO 86
<211> LENGTH: 10
<212> TYPE: PRT
<213> ORGANISM: Unknown
<220> FEATURE:
<221> NAME/KEY: DOMAIN
<223> OTHER INFORMATION: Motif VI of RNA guanylyltransferase from
      AcNPV baculovirus

<400> SEQUENCE: 86

Ile Asn Val Leu Lys His Arg Arg Asp Arg
                5                  10

<210> SEQ ID NO 87
<211> LENGTH: 6
<212> TYPE: PRT
<213> ORGANISM: Plasmodium falciparum
<220> FEATURE:
<221> NAME/KEY: DOMAIN
<223> OTHER INFORMATION: Motif I of RNA guanylyltransferase from
      Plasmodium falciparum

<400> SEQUENCE: 87

Lys Thr Asp Gly Val Arg
                5

<210> SEQ ID NO 88
<211> LENGTH: 8
<212> TYPE: PRT
<213> ORGANISM: Plasmodium falciparum
<220> FEATURE:
<221> NAME/KEY: DOMAIN
<223> OTHER INFORMATION: Motif III of RNA guanylyltransferase from
      Plasmodium falciparum

<400> SEQUENCE: 88

Thr Leu Leu Asp Gly Glu Leu Val
                5

<210> SEQ ID NO 89
<211> LENGTH: 12
<212> TYPE: PRT
<213> ORGANISM: Plasmodium falciparum
<220> FEATURE:
<221> NAME/KEY: DOMAIN
<223> OTHER INFORMATION: Motif IIIa of RNA guanylyltransferase from
      Plasmodium falciparum

<400> SEQUENCE: 89

Val Tyr Leu Ile Tyr Asp Gly Leu Tyr Ile Gln Arg
                5                  10

<210> SEQ ID NO 90
<211> LENGTH: 5
<212> TYPE: PRT
<213> ORGANISM: Plasmodium falciparum
<220> FEATURE:
<221> NAME/KEY: DOMAIN
<223> OTHER INFORMATION: Motif IV of RNA guanylyltransferase from
      Plasmodium falciparum

<400> SEQUENCE: 90

Asp Gly Ile Ile Phe
              5

<210> SEQ ID NO 91
<211> LENGTH: 13
<212> TYPE: PRT
<213> ORGANISM: Plasmodium falciparum
<220> FEATURE:
<221> NAME/KEY: DOMAIN
<223> OTHER INFORMATION: Motif V of RNA guanylyltransferase from
      Plasmodium falciparum

<400> SEQUENCE: 91

Leu Leu Lys Trp Lys Pro Leu Asn Leu Asn Thr Val Asp
                5                  10

<210> SEQ ID NO 92
<211> LENGTH: 10
<212> TYPE: PRT
<213> ORGANISM: Plasmodium falciparum
<220> FEATURE:
<221> NAME/KEY: DOMAIN
<223> OTHER INFORMATION: Motif VI of RNA guanylyltransferase from
      Plasmodium falciparum

<400> SEQUENCE: 92

Trp Ile Ala Gln Lys Ile Arg Phe Asp Lys
                5                  10

<210> SEQ ID NO 93
<211> LENGTH: 195
<212> TYPE: PRT
<213> ORGANISM: Unknown
<220> FEATURE:
<221> NAME/KEY: DOMAIN
<223> OTHER INFORMATION: RNA triphosphatase domain of mammalian capping
      enzyme Mce1

<400> SEQUENCE: 93

Lys Ile Pro Pro Arg Trp Leu Asn Cys Pro Arg Arg Gly Gln Pro
                5                  10                  15

Val Ala Gly Arg Phe Leu Pro Leu Lys Thr Met Leu Gly Pro Arg
                20                 25                  30

Tyr Asp Ser Gln Val Ala Glu Glu Asn Arg Phe His Pro Ser Met
                35                 40                  45

Leu Ser Asn Tyr Leu Lys Ser Leu Lys Val Lys Met Ser Leu Leu
                50                 55                  60

Val Asp Leu Thr Asn Thr Ser Arg Phe Tyr Asp Arg Asn Asp Ile
                65                 70                  75

Glu Lys Glu Gly Ile Lys Tyr Ile Lys Leu Gln Cys Lys Gly His
                80                 85                  90

Gly Glu Cys Pro Thr Thr Glu Asn Thr Glu Thr Phe Ile Arg Leu

-continued

```
                 95                 100                 105

Cys Glu Arg Phe Asn Glu Arg Ser Pro Pro Glu Leu Ile Gly Val
            110                 115                 120

His Cys Thr His Gly Phe Asn Arg Thr Gly Phe Leu Ile Cys Ala
            125                 130                 135

Phe Leu Val Glu Lys Met Asp Trp Ser Ile Glu Ala Ala Val Ala
            140                 145                 150

Thr Phe Ala Gln Ala Arg Pro Pro Gly Ile Tyr Lys Gly Asp Tyr
            155                 160                 165

Leu Lys Glu Leu Phe Arg Arg Tyr Gly Asp Ile Glu Glu Ala Pro
            170                 175                 180

Pro Pro Pro Val Leu Pro Asp Trp Cys Phe Glu Asp Glu Asp Glu
            185                 190                 195
```

<210> SEQ ID NO 94
<211> LENGTH: 197
<212> TYPE: PRT
<213> ORGANISM: C elegans
<220> FEATURE:
<221> NAME/KEY: DOMAIN
<223> OTHER INFORMATION: RNA triphosphatase domain of C elegans RNA
      capping enzyme

<400> SEQUENCE: 94

```
Gly Leu Pro Asp Arg Trp Leu His Cys Pro Lys Thr Gly Thr Leu
              5                  10                  15

Ile Asn Asn Leu Phe Phe Pro Phe Lys Thr Pro Leu Cys Lys Met
             20                  25                  30

Tyr Asp Asn Gln Ile Ala Glu Arg Arg Tyr Gln Phe His Pro Ala
             35                  40                  45

Glu Val Phe Ser His Pro His Leu His Gly Lys Lys Ile Gly Leu
             50                  55                  60

Trp Ile Asp Leu Thr Asn Thr Asp Arg Tyr Tyr Phe Arg Glu Glu
             65                  70                  75

Val Thr Glu His Glu Cys Ile Tyr His Lys Met Lys Met Ala Gly
             80                  85                  90

Arg Gly Val Ser Pro Thr Gln Glu Asp Thr Asp Asn Phe Ile Lys
             95                 100                 105

Leu Val Gln Glu Phe His Lys Lys Tyr Pro Asp Arg Val Val Gly
            110                 115                 120

Val His Cys Thr His Gly Phe Asn Arg Thr Gly Phe Leu Ile Ala
            125                 130                 135

Ala Tyr Leu Phe Gln Val Glu Glu Tyr Gly Leu Asp Ala Ala Ile
            140                 145                 150

Gly Glu Phe Ala Glu Asn Arg Gln Lys Gly Ile Tyr Lys Gln Asp
            155                 160                 165

Tyr Ile Asp Asp Leu Phe Ala Arg Tyr Asp Pro Thr Glu Asp Asp
            170                 175                 180

Lys Ile Leu Ala Pro Glu Lys Pro Asp Trp Glu Arg Glu Met Ser
            185                 190                 195

Ile Gly
    197
```

<210> SEQ ID NO 95
<211> LENGTH: 196
<212> TYPE: PRT
<213> ORGANISM: Drosophila melanogaster

```
<220> FEATURE:
<221> NAME/KEY: DOMAIN
<223> OTHER INFORMATION: RNA triphosphatase domain of
      Drosophila melanogaster RNA capping enzyme

<400> SEQUENCE: 95

Pro Leu Pro Asn Arg Trp Leu Tyr Cys Pro Arg Lys Ser Asp Thr
                 5                  10                  15

Ile Ile Ala Glu Arg Phe Leu Ala Phe Lys Thr Pro Leu Ser Asn
             20                  25                  30

Asn Phe His Asp Lys Met Pro Ile Glu Cys Thr Phe Gln Pro Glu
             35                  40                  45

Met Leu Phe Glu Tyr Cys Lys Thr Leu Lys Val Lys Leu Gly Leu
             50                  55                  60

Trp Val Asp Leu Thr Asn Thr Lys Arg Phe Tyr Asp Arg Ser Ala
             65                  70                  75

Val Glu Glu Leu Gly Ala Lys Tyr Ile Lys Leu Gln Cys Arg Gly
             80                  85                  90

His Gly Glu Thr Pro Ser Pro Glu Gln Thr His Ser Phe Ile Glu
             95                 100                 105

Ile Val Asp Asn Phe Ile Asn Glu Arg Pro Phe Asp Val Ile Ala
            110                 115                 120

Val His Cys Thr His Gly Phe Asn Arg Thr Gly Phe Leu Ile Val
            125                 130                 135

Cys Tyr Leu Val Glu Arg Leu Asp Cys Ser Val Ser Ala Ala Leu
            140                 145                 150

Ala Ile Phe Ala Ser Ala Arg Pro Pro Gly Ile Tyr Lys Gln Asp
            155                 160                 165

Tyr Ile Asn Glu Leu Tyr Lys Arg Tyr Glu Asp Thr Asn Ala Ala
            170                 175                 180

Pro Ala Ala Pro Glu Gln Pro Asn Trp Cys Leu Asp Tyr Asp Asp
            185                 190                 195

Gly
196

<210> SEQ ID NO 96
<211> LENGTH: 195
<212> TYPE: PRT
<213> ORGANISM: Xenopus laevis
<220> FEATURE:
<221> NAME/KEY: DOMAIN
<223> OTHER INFORMATION: RNA triphosphatase domain of Xenopus laevis
      RNA capping enzyme

<400> SEQUENCE: 96

Lys Ile Pro Pro Arg Trp Leu Asn Cys Pro Arg Arg Gly Gln Pro
                 5                  10                  15

Val Ala Gly Arg Phe Leu Pro Leu Lys Thr Ile Leu Gly Pro Arg
             20                  25                  30

Tyr Asp Ser Gln Val Ala Glu Glu Asn Arg Phe His Pro Ser Met
             35                  40                  45

Leu Ser Asn Tyr Leu Lys Ser Leu Lys Val Lys Met Gly Leu Leu
             50                  55                  60

Val Asp Leu Thr Asn Thr Ser Arg Phe Tyr Asp Arg Asn Asp Ile
             65                  70                  75

Glu Lys Glu Gly Ile Lys Tyr Ile Lys Leu Gln Cys Lys Gly His
             80                  85                  90
```

-continued

```
Gly Glu Cys Pro Thr Thr Glu Asn Thr Glu Thr Phe Ile Arg Leu
                 95                 100                 105

Cys Glu Arg Phe Asn Glu Arg Asn Pro Pro Glu Leu Ile Gly Val
                110                 115                 120

His Cys Thr His Gly Phe Asn Arg Thr Gly Phe Leu Ile Cys Ala
                125                 130                 135

Phe Leu Val Glu Lys Met Asp Trp Ser Ile Glu Ala Ala Val Ala
                140                 145                 150

Thr Phe Ala Gln Ala Arg Pro Pro Gly Ile Tyr Lys Gly Asp Tyr
                155                 160                 165

Leu Lys Glu Leu Phe Arg Arg Tyr Gly Asp Ile Glu Asp Ala Pro
                170                 175                 180

Lys Pro Pro Glu Leu Pro Asp Trp Cys Phe Glu Glu Glu Asp Val
                185                 190                 195

<210> SEQ ID NO 97
<211> LENGTH: 197
<212> TYPE: PRT
<213> ORGANISM: Arabidopsis thaliana
<220> FEATURE:
<221> NAME/KEY: DOMAIN
<223> OTHER INFORMATION: RNA triphosphatase domain of
      Arabidopsis thaliana RNA capping enzyme

<400> SEQUENCE: 97

Lys Ile Pro Gln Gly Trp Leu Asp Cys Pro Pro Ser Gly Asn Glu
                 5                  10                  15

Ile Gly Phe Leu Val Pro Ser Lys Val Pro Leu Asn Glu Ser Tyr
                20                  25                  30

Asn Asn His Val Pro Pro Gly Ser Arg Tyr Ser Phe Lys Gln Val
                35                  40                  45

Ile His Asn Gln Arg Ile Ala Gly Arg Lys Leu Gly Leu Val Ile
                50                  55                  60

Asp Leu Thr Asn Thr Thr Arg Tyr Tyr Ser Thr Thr Asp Leu Lys
                65                  70                  75

Lys Glu Gly Ile Lys His Val Lys Ile Ala Cys Lys Gly Arg Asp
                80                  85                  90

Ala Val Pro Asp Asn Val Ser Val Asn Ala Phe Val Asn Glu Val
                95                  100                 105

Asn Gln Phe Val Leu Asn Leu Lys His Ser Lys Lys Tyr Ile Leu
                110                 115                 120

Val His Cys Thr His Gly His Asn Arg Thr Gly Phe Met Ile Val
                125                 130                 135

His Tyr Leu Met Arg Ser Gly Pro Met Asn Val Thr Gln Ala Leu
                140                 145                 150

Lys Ile Phe Ser Asp Ala Arg Pro Pro Gly Ile Tyr Lys Pro Asp
                155                 160                 165

Tyr Ile Asp Ala Leu Tyr Ser Phe Tyr His Glu Ile Lys Pro Glu
                170                 175                 180

Ser Val Ile Cys Pro Ser Thr Pro Glu Trp Lys Arg Ser Thr Glu
                185                 190                 195

Leu Asp
    197

<210> SEQ ID NO 98
<211> LENGTH: 186
<212> TYPE: PRT
```

<213> ORGANISM: Homo sapiens
<220> FEATURE:
<221> NAME/KEY: DOMAIN
<223> OTHER INFORMATION: Human RNA-specific 5' phosphatase PIR1

<400> SEQUENCE: 98

```
His Ile Pro Glu Arg Trp Lys Asp Tyr Leu Pro Val Gly Gln Arg
                5                  10                  15
Met Pro Gly Thr Arg Phe Ile Ala Phe Lys Val Pro Leu Gln Lys
            20                  25                  30
Ser Phe Glu Lys Lys Leu Ala Pro Glu Cys Phe Ser Pro Leu
        35                  40                  45
Asp Leu Phe Asn Lys Ile Arg Glu Gln Asn Glu Leu Gly Leu
    50                  55                  60
Ile Ile Asp Leu Thr Tyr Thr Gln Arg Tyr Tyr Lys Pro Glu Asp
                65                  70                  75
Leu Pro Glu Thr Val Pro Tyr Leu Lys Ile Phe Thr Val Gly His
            80                  85                  90
Gln Val Pro Asp Asp Glu Thr Ile Phe Lys Phe Lys His Ala Val
        95                  100                 105
Asn Gly Phe Leu Lys Glu Asn Lys Asp Asn Asp Lys Leu Ile Gly
        110                 115                 120
Val His Cys Thr His Gly Leu Asn Arg Thr Gly Tyr Leu Ile Cys
        125                 130                 135
Arg Tyr Leu Ile Asp Val Glu Gly Val Arg Pro Asp Asp Ala Ile
        140                 145                 150
Glu Leu Phe Asn Arg Cys Arg Gly His Cys Leu Glu Arg Gln Asn
        155                 160                 165
Tyr Ile Glu Asp Leu Gln Asn Gly Pro Ile Arg Lys Asn Trp Asn
        170                 175                 180
Ser Ser Val Pro Arg Ser
            185
```

<210> SEQ ID NO 99
<211> LENGTH: 168
<212> TYPE: PRT
<213> ORGANISM: Unknown
<220> FEATURE:
<221> NAME/KEY: DOMAIN
<223> OTHER INFORMATION: Baculovirus RNA-specific 5' phosphatase BVP

<400> SEQUENCE: 99

```
Met Phe Pro Ala Arg Trp His Asn Tyr Leu Gln Cys Gly Gln Val
                5                  10                  15
Ile Lys Asp Ser Asn Leu Ile Cys Phe Lys Thr Pro Leu Arg Pro
            20                  25                  30
Glu Leu Phe Ala Tyr Val Thr Ser Glu Asp Val Trp Thr Ala
        35                  40                  45
Glu Gln Ile Val Lys Gln Asn Pro Ser Ile Gly Ala Ile Asp
    50                  55                  60
Leu Thr Asn Thr Ser Lys Tyr Tyr Asp Gly Val His Phe Leu Arg
                65                  70                  75
Ala Gly Leu Leu Tyr Lys Lys Ile Gln Val Pro Gly Gln Thr Leu
            80                  85                  90
Pro Pro Glu Ser Ile Val Gln Glu Phe Ile Asp Thr Val Lys Glu
        95                  100                 105
Phe Thr Glu Lys Cys Pro Gly Met Leu Val Gly Val His Cys Thr
```

-continued

```
                    110                 115                 120
His Gly Ile Asn Arg Thr Gly Tyr Met Val Cys Arg Tyr Leu Met
                    125                 130                 135

His Thr Leu Gly Ile Ala Pro Gln Glu Ala Ile Asp Arg Phe Glu
                    140                 145                 150

Lys Ala Arg Gly His Lys Ile Glu Arg Gln Asn Tyr Val Gln Asp
                    155                 160                 165

Leu Leu Ile
        168
```

<210> SEQ ID NO 100
<211> LENGTH: 236
<212> TYPE: PRT
<213> ORGANISM: Saccharomyces cerevisiae
<220> FEATURE:
<221> NAME/KEY: DOMAIN
<223> OTHER INFORMATION: Catalytic domain of RNA triphosphatase from
      S. cerevisiae Cet1

<400> SEQUENCE: 100

```
Ile Glu Leu Glu Met Lys Phe Gly Val Ile Ile Asp Ala Lys Gly
                    5                   10                  15

Pro Asp Arg Val Asn Pro Val Ser Ser Gln Cys Val Phe Thr
                    20                  25                  30

Glu Leu Asp Ala His Leu Thr Pro Asn Ile Asp Ala Ser Leu Phe
                    35                  40                  45

Lys Glu Leu Ser Lys Tyr Ile Arg Gly Ile Ser Glu Val Thr Glu
                    50                  55                  60

Asn Thr Gly Lys Phe Ser Ile Ile Glu Ser Gln Thr Arg Asp Ser
                    65                  70                  75

Val Tyr Arg Val Gly Leu Ser Thr Gln Arg Pro Arg Phe Leu Arg
                    80                  85                  90

Met Ser Thr Asp Ile Lys Thr Gly Arg Val Gly Gln Phe Ile Glu
                    95                  100                 105

Lys Arg His Val Ala Gln Leu Leu Leu Tyr Ser Pro Lys Asp Ser
                    110                 115                 120

Tyr Asp Val Lys Ile Ser Leu Asn Leu Glu Leu Pro Val Pro Asp
                    125                 130                 135

Asn Asp Pro Pro Glu Lys Tyr Lys Ser Gln Ser Pro Ile Ser Glu
                    140                 145                 150

Arg Thr Lys Asp Arg Val Ser Tyr Ile His Asn Asp Ser Cys Thr
                    155                 160                 165

Arg Ile Asp Ile Thr Lys Val Glu Asn His Asn Gln Asn Ser Lys
                    170                 175                 180

Ser Arg Gln Ser Glu Thr Thr His Glu Val Glu Leu Glu Ile Asn
                    185                 190                 195

Thr Pro Ala Leu Leu Asn Ala Phe Asp Asn Ile Thr Asn Asp Ser
                    200                 205                 210

Lys Glu Tyr Ala Ser Leu Ile Arg Thr Phe Leu Asn Asn Gly Thr
                    215                 220                 225

Ile Ile Arg Arg Lys Leu Ser Ser Leu Ser Tyr
                    230                 235
```

<210> SEQ ID NO 101
<211> LENGTH: 235
<212> TYPE: PRT
<213> ORGANISM: Candida albicans

```
<220> FEATURE:
<221> NAME/KEY: DOMAIN
<223> OTHER INFORMATION: Catalytic domain of RNA triphosphatase from
      Candida albicans CaCet1

<400> SEQUENCE: 101
```

Val Glu Leu Glu Leu Lys Phe Gly Lys Ile Ile Asp Lys Arg Ser
              5                  10                  15

Gly Asn Arg Ile Asp Leu Asn Val Val Thr Glu Cys Ile Phe Thr
             20                  25                  30

Asp His Ser Ser Val Phe Phe Asp Met Gln Val Glu Glu Val Ala
             35                  40                  45

Trp Lys Glu Ile Thr Lys Phe Leu Asp Glu Leu Glu Lys Ser Phe
             50                  55                  60

Gln Glu Gly Lys Lys Gly Arg Lys Phe Lys Thr Leu Glu Ser Asp
             65                  70                  75

Asn Thr Asp Ser Phe Tyr Gln Leu Gly Arg Lys Gly Glu His Pro
             80                  85                  90

Lys Arg Ile Arg Val Thr Lys Asp Asn Leu Leu Ser Pro Pro Arg
             95                 100                 105

Leu Val Ala Ile Gln Lys Glu Arg Val Ala Asp Leu Tyr Ile His
            110                 115                 120

Asn Pro Gly Ser Leu Phe Asp Leu Arg Leu Ser Met Ser Leu Glu
            125                 130                 135

Ile Pro Val Pro Gln Gly Asn Ile Glu Ser Ile Ile Thr Lys Asn
            140                 145                 150

Lys Pro Glu Met Val Arg Glu Lys Lys Arg Ile Ser Tyr Thr His
            155                 160                 165

Pro Pro Thr Ile Thr Lys Phe Asp Leu Thr Arg Val Ile Gly Asn
            170                 175                 180

Lys Thr Glu Asp Lys Tyr Glu Val Glu Leu Glu Ala Gly Val Met
            185                 190                 195

Glu Ile Phe Ala Ala Ile Asp Lys Ile Gln Lys Gly Val Asp Asn
            200                 205                 210

Leu Arg Leu Glu Glu Leu Ile Glu Val Phe Leu Asn Asn Ala Arg
            215                 220                 225

Thr Leu Asn Asn Arg Leu Asn Lys Ile Cys
            230                 235

```
<210> SEQ ID NO 102
<211> LENGTH: 232
<212> TYPE: PRT
<213> ORGANISM: Saccharomyces cerevisiae
<220> FEATURE:
<221> NAME/KEY: DOMAIN
<223> OTHER INFORMATION: Catalytic domain of RNA triphosphatase from
      S. cerevisiae  Cth1

<400> SEQUENCE: 102
```

Ile Glu Ile Glu Met Lys Phe Gly Val Ile Thr Asp Lys Arg Thr
              5                  10                  15

His Arg Arg Met Thr Pro His Asn Lys Pro Phe Ile Val Gln Asn
             20                  25                  30

Arg Asn Gly Arg Leu Val Ser Asn Val Pro Glu Gln Met Phe Ser
             35                  40                  45

Ser Phe Gln Glu Leu Leu Arg Ser Lys Ser Glu Asn Pro Ser Lys
             50                  55                  60

```
Cys Ala Pro Arg Val Val Lys Gln Val Gln Lys Tyr Thr Lys Asp
                 65                  70                  75

Ser Ile Tyr Asn Cys Asn Asn Ala Ser Lys Val Gly Lys Leu Thr
             80                  85                  90

Ser Trp Arg Cys Ser Glu Asp Leu Arg Asn Lys Glu Leu Lys Leu
             95                 100                 105

Thr Tyr Ile Lys Lys Val Arg Val Lys Asp Phe Leu Ile Arg Tyr
            110                 115                 120

Pro Gln Ser Ser Leu Asp Ala Lys Ile Ser Ile Ser Leu Glu Val
            125                 130                 135

Pro Glu Tyr Glu Thr Ser Ala Ala Phe Arg Asn Gly Phe Ile Leu
            140                 145                 150

Gln Arg Thr Lys Ser Arg Ser Thr Tyr Thr Phe Asn Asp Lys Met
            155                 160                 165

Pro Leu His Leu Asp Leu Thr Lys Val Thr Thr Thr Arg Arg Asn
            170                 175                 180

Ser His Gln Tyr Thr Ser His Glu Val Glu Val Met Asp Pro
            185                 190                 195

Ile Phe Lys Glu Thr Ile Ser Ala Asn Asp Arg Glu Lys Phe Asn
            200                 205                 210

Glu Tyr Met Cys Ser Phe Leu Asn Ala Ser Asp Leu Ile Arg Lys
            215                 220                 225

Ala Ala Glu Arg Asp Asn Met
            230

<210> SEQ ID NO 103
<211> LENGTH: 227
<212> TYPE: PRT
<213> ORGANISM: Schizosaccharomyces pombe
<220> FEATURE:
<221> NAME/KEY: DOMAIN
<223> OTHER INFORMATION: Catalytic domain of RNA triphosphatase from
      S. pombe Pct1

<400> SEQUENCE: 103

Val Glu Ile Glu Ala Lys Leu Gly Thr Leu Ile Asp Leu Glu Thr
                 5                  10                  15

Gln Asn Arg Phe Glu Phe Pro Val Met Asn Glu Thr Ile Leu Asn
             20                  25                  30

Pro Glu Phe Asn Leu Arg Thr Arg Phe Glu Ser Asp Met Thr Ala
             35                  40                  45

Ser Glu His Lys Tyr Leu Asn Glu Phe Leu Asn Gln Ala Phe Arg
             50                  55                  60

Asp Ser Gln Lys Pro Gly Arg Leu Pro Phe Ala Tyr Lys His Thr
             65                  70                  75

Lys Gln Val Asp Leu Phe Tyr Glu Thr Glu Asp Asn Ser Arg Asp
             80                  85                  90

Lys Ile Arg Val Ser Lys Asn Gln Ser Asp Asn Gln Val Leu Ala
             95                 100                 105

Cys Val Lys Lys Arg Arg Val Ala Asp Leu Phe Leu Tyr Cys Pro
            110                 115                 120

Asn Asp Ala Phe Asp Ile Arg Ile Ser Ile Ser Asp Glu Leu Pro
            125                 130                 135

Val Ser Met Pro Ser Gly Asn Gln Gln Pro Ser Leu Thr Arg Leu
            140                 145                 150

Lys Asp Arg Val Gly Tyr Val His Gln Glu Ile Lys Ile Asp Leu
```

-continued

```
                    155                 160                 165
Thr Lys Thr Thr Gln Asn Asp Pro Val Tyr Asp Thr Glu Arg
                170                 175                 180
His Glu Leu Glu Val Glu Phe Gly Asn Ile Ala Asp Leu Arg Asp
                185                 190                 195
Arg Ala Gln Lys Ala Lys Asp Gly Met Glu Ala Pro Leu Phe Arg
                200                 205                 210
Arg Val Gln Leu Phe Met Asp Asn Val Arg Ile Leu Arg Arg Glu
                215                 220                 225
His Ser
    227

<210> SEQ ID NO 104
<211> LENGTH: 193
<212> TYPE: PRT
<213> ORGANISM: Plasmodium falciparum
<220> FEATURE:
<221> NAME/KEY: DOMAIN
<223> OTHER INFORMATION: Catalytic domain of RNA triphosphatase from
      Plasmodium falciparum RNA triphosphatase Prt1

<400> SEQUENCE: 104

Ile Glu Ile Glu Gly Arg Val Gly Leu Val Ile Asp Lys Asn Lys
                  5                  10                  15
Asn Arg Ile Lys Leu Pro Ile Asn Thr Asp Ala Ile Ile Glu Asn
                 20                  25                  30
Asn Tyr Ser Asp Phe Gln Ala Gly Ile Asp Arg Glu Ser Phe Glu
                 35                  40                  45
Tyr Leu Leu Asp Tyr Phe His Asn Met Thr Leu Lys Lys Arg Leu
                 50                  55                  60
Ser Ile Arg Asn Asn Asn Thr His Gly Leu Thr Thr Ser Lys
                 65                  70                  75
Ser Gln His Ile Tyr Asn Asn Leu Val Asp Lys Asn Asp Ser Ile
                 80                  85                  90
Asp Tyr Arg Ile Ser Ile Asn Ile Glu Tyr Thr Lys Pro Ile Ser
                 95                 100                 105
Lys Leu Tyr Leu Ser Lys Asn Thr Pro Val His Glu Arg Leu Lys
                110                 115                 120
Glu Arg Thr Thr Phe Ile Asn Thr Tyr Leu Gly Leu Gln Val Asp
                125                 130                 135
Met Thr Lys Ile Lys Thr Lys Asn Asn Glu Leu Tyr Glu Val Glu
                140                 145                 150
Ile Glu Ile Pro Ser Lys Thr Ile Phe Lys Ala Met Ser Asn Leu
                155                 160                 165
Arg Asn Lys Lys Asp Ser Asn Tyr Leu His Phe Ile Cys Ser Asn
                170                 175                 180
Leu Val Asn Asn Ile Arg Gly Ile Cys Ser Gln Leu Asn
                185                 190
```

PHARMACOLOGICAL TARGETING OF MRNA CAP FORMATION FOR TREATMENT OF PARASITIC INFECTIONS

This is a divisional application of application No. 09/752,165, filed Dec. 29, 2000, now U.S. Pat. No. 6,451,583.

BACKGROUND OF THE INVENTION

1. Field of the Invention

The present invention relates generally to the fields of biochemical pharmacology and drug discovery. More specifically, the present invention relates to the novel mRNA capping enzymes Pgt1 and Prt1 from *Plasmodium falciparum*, the agent of malaria, and methods of screening for antimalarial and antiprotozoal compounds that inhibit mRNA cap formation.

2. Description of the Related Art

Malaria extracts a prodigious toll each year in human morbidity (400 million new cases) and mortality (1 million deaths). The malaria parasite is transmitted when humans are bitten by the Anopheles mosquito. Of the four species of Plasmodium parasites that cause human malaria—*Plasmodium vivax, Plasmodium malariae, Plasmodium ovale*, and *Plasmodium falciparum*—it is *P. falciparum* that is principally responsible for fulminant disease and death. Malaria treatment and prevention strategies have been steadily undermined by the spreading resistance of the Plasmodium pathogen to erstwhile effective drugs and of the mosquito vector to insecticides [1]. Thus, there is an acute need for new malaria therapies.

It is anticipated that the *Plasmodium falciparum* genome project [2] will uncover novel targets for therapy and immunization. The most promising drug targets will be those gene products or metabolic pathways that are essential for all stages of the parasite life cycle, but either absent or fundamentally different in the human host and the arthropod vector. Such targets can be identified either by whole-genome comparisons or by directed analyses of specific cellular transactions. In those instances where Plasmodium differs from metazoans, comparisons to other unicellular organisms may provide insights into eukaryotic phylogeny.

Processing of eukaryotic mRNA in vivo is coordinated temporally and physically with transcription. The earliest event is the modification of the 5' terminus of the nascent transcript to form the cap structure m7GpppN. The cap is formed by three enzymatic reactions: (i) the 5' triphosphate end of the nascent RNA is hydrolyzed to a diphosphate by RNA 5' triphosphatase; (ii) the diphosphate end is capped with GMP by GTP:RNA guanylyltransferase; and (iii) the GpppN cap is methylated by AdoMet:RNA (guanine-N7) methyltransferase [3].

RNA capping is essential for cell growth. Mutations of the triphosphatase, guanylyltransferase, or methyltransferase components of the yeast capping apparatus that abrogate catalytic activity are lethal in vivo. Genetic and biochemical experiments highlight roles for the cap in protecting mRNA from untimely degradation by cellular 5' exonucleases and in recruiting the mRNA to the ribosome during translation initiation.

The physical and functional organizations of the capping apparatus differ in significant respects in metazoans, fungi, and viruses. Mammals and other metazoa encode a two-component capping system consisting of a bifunctional triphosphatase-guanylyltransferase polypeptide and a separate methyltransferase polypeptide. Fungi encode a three-component system consisting of separate triphosphatase, guanylyltransferase, and methyltransferase gene products. Viral capping systems are quite variable in their organization; poxviruses encode a single polypeptide containing all three active sites, whereas phycodnaviruses encode a yeast-like capping apparatus in which the triphosphatase and guanylyltransferase enzymes are encoded separately [4].

The guanylyltransferase and methyltransferase components of the capping apparatus are mechanistically conserved between metazoans and budding yeast. In contrast, the structures and catalytic mechanisms of the mammalian and fungal RNA triphosphatases are completely different [5]. The triphosphatase components of many viral mRNA capping enzymes are mechanistically and structurally related to the fungal RNA triphosphatases and not to the host cell triphosphatase [4, 6, 7]. Thus, cap formation and cap-forming enzymes, especially RNA triphosphatase, are promising targets for antifungal and antiviral drug discovery.

A plausible strategy for antimalarial drug discovery is to identify compounds that block Plasmodium-encoded capping activities without affecting the capping enzymes of the human host or the mosquito vector. For this approach to be feasible, the capping enzymes of the malaria parasite must be identified.

Little is known about the organization of the mRNA capping apparatus in the many other branches of the eukaryotic phylogenetic tree. RNA guanylyltransferase has been studied in the kinetoplastids Trypanosoma and Crithidia [8] but the triphosphatase and methyltransferase components have not been identified.

RNA Guanylyltransferase—Transfer of GMP from GTP to the 5' diphosphate terminus of RNA occurs in a two-step reaction involving a covalent enzyme-GMP intermediate [3]. Both steps require a divalent cation cofactor.

(i) E+pppG<>E-pG+PPi (ii) E-pG+ppRNA<>GpppRNA+E

The GMP is covalently linked to the enzyme through a phosphoamide (P—N) bond to the epsilon-amino group of a lysine residue within a conserved KxDG element (motif I) found in all known cellular and DNA virus-encoded capping enzymes (FIG. 1). Five other sequence motifs (III, IIIa, IV, V, and VI) are conserved in the same order and with similar spacing in the capping enzymes from fungi, metazoans, DNA viruses, and trypanosomes (FIG. 1) [3].

Håkansson et al. [9] have determined the crystal structure of the Chlorella virus guanylyltransferase in the GTP-bound state and with GMP bound covalently. The protein consist of a larger N-terminal domain (domain 1, containing motifs I, III, IIIa, and IV) and a smaller C-terminal domain (domain 2, containing motif VI) with a deep cleft between them. Motif V bridges the two domains. Motifs I, III, IIIa, IV, and V form the nucleotide binding pocket. The crystal structure reveals a large conformational change in the GTP-bound enzyme, from an "open" to a "closed" state, that brings motif VI into contact with the beta and gamma phosphates of GTP and reorients the phosphates for in-line attack by the motif I lysine.

Identification of essential amino acids has been accomplished by site-directed mutagenesis of Ceg1 the RNA guanylyltransferase of *Saccharomyces cerevisiae*. The guanylyltransferase activity of Ceg1p is essential for cell viability. Hence, mutational effects on Ceg1 function in vivo can be evaluated by simple exchange of mutant CEG1 alleles for the wild type gene. The effects of alanine substitutions for individual amino acids in motifs I, III, IIIa, IV, V, and VI have been examined. Sixteen residues were defined as essential (denoted by dots in FIG. 1) and structure-activity relationships at these positions were subsequently determined by conservative replacements [10]. Many of the essential Ceg1 side chains correspond to moieties which, in the Chlorella virus capping enzyme crystal structure, make direct contact with GTP as denoted by the arrowheads in FIG. 1.

RNA Triphosphatase—There are at least two mechanistically and structurally distinct classes of RNA 5' triphosphatases: (i) the divalent cation-dependent RNA triphosphatase/NTPase family (exemplified by *Saccharomyces cerevisiae* Cet1 and Cth1, *Candida albicans* CaCet1, *Schizosaccharomyces pombe* Pct1, Chlorella virus Rtp1, baculovirus LEF-4, and vaccinia virus, D1), which require three conserved collinear motifs (A, B, and C) for activity [4,6,7,11-14], and (ii) the divalent cation-independent RNA triphosphatases, e.g., the metazoan cellular mRNA capping enzymes, the baculovirus phosphatase BVP, and the human enzyme PIR1, which require a HCxxxxxR(S/T) phosphate-binding motif [15–17].

Metazoan capping enzymes consist of an N-terminal RNA triphosphatase domain and a C-terminal guanylyltransferase domain. In the 497-amino acid mouse enzyme Mce1, the two catalytic domains are autonomous and nonoverlapping [15]. The metazoan RNA triphosphatases belong to a superfamily of cysteine phosphatases that includes protein tyrosine phosphatases, dual specificity protein phosphatases, and phosphoinositide phosphatases. The metazoan RNA triphosphatases contain a HCxxxxxR(S/T) signature motif (referred to as the P loop) that defines the cysteine phosphatase superfamily (FIG. 2). Metazoan RNA triphosphatases catalyze the cleavage of the γ phosphate of 5' triphosphate RNA via a two-step pathway. First, a cysteine thiolate nucleophile of the enzyme (the conserved cysteine of the P loop) attacks the γ phosphorus to form a covalent protein-cysteinyl-S-phosphate intermediate [16] and release the diphosphate-terminated product. Then the covalent intermediate is hydrolyzed to liberate inorganic phosphate. The metazoan RNA triphosphatases do not require a metal cofactor.

*Saccharomyces cerevisiae* Cet1 exemplifies the class of divalent cation-dependent RNA triphosphatase enzymes, which includes the RNA triphosphatase encoded by the pathogenic fungus *Candida albicans*, the fission yeast *Schizosaccharomyces pombe*, and the RNA triphosphatase components of the capping systems of poxviruses, baculoviruses, and Chlorella virus PBCV-1. This triphosphatase family is defined by three conserved collinear motifs (A, B, and C) that include clusters of acidic and basic amino acids that are essential for Cet1 catalytic activity [6,12] (FIG. 3).

Purified recombinant Cet1 catalyzes the magnesium-dependent hydrolysis of the γ phosphate of triphosphate-terminated RNA to form a 5' diphosphate end. Cet1 also displays a robust ATPase activity in the presence of manganese or cobalt, but magnesium, calcium, copper, and zinc are not effective cofactors for ATP hydrolysis [6]. Cet1 displays broad specificity in converting rNTPs and dNTPs to their respective diphosphates. The manganese- and cobalt-dependent NTPase activity of Cet1 resembles the manganese- or cobalt-dependent NTPase activities of the of the other members of this family, including baculovirus LEF-4, *C. albicans* CaCet1, *S. cerevisiae* Cth1, *S. pombe* Pct1, and Chlorella virus Rtp1 [4,11–14].

Crystal Structure of Fungal RNA Triphosphatase—The biologically active triphosphatase derivative Cet1(241–539) was crystallized and its structure determined at 2.05 Å resolution [5]. Consistent with solution studies, Cet1 crystallized as a dimer. The striking feature of the tertiary structure is the formation of a topologically closed tunnel composed of 8 antiparallel β strands. The active site resides within this hydrophilic "triphosphate tunnel". The β strands that comprise the walls of the tunnel are displayed over the Cet1 protein sequence in FIG. 3. The interior of the tunnel contained a single sulfate ion coordinated by two arginine and two lysine side chains. Insofar as sulfate is a structural analog of phosphate, it is likely that the side chain interactions of the sulfate reflect contacts made by the enzyme with the γ phosphate of the triphosphate-terminated RNA and nucleoside triphosphate substrates.

The proteins most closely related to Cet1 at the primary structure level are CaCet1, Pct1, and Cth1. CaCet1 is the RNA triphosphatase component of the capping apparatus of *Candida albicans*. Pct1 is the RNA triphosphatase component of the capping apparatus of *Schizosaccharomyces pombe* [14]. Cth1 is a nonessential *S. cerevisiae* protein with divalent cation-dependent RNA triphosphatase/NTPase activity that may participate in an RNA transaction unrelated to capping [12]. The amino acid sequences of Cet1, CaCet1, Pct1, and Cth1 are aligned in FIG. 3. The residues conserved in all four fungal enzymes are localized predominantly in the interior of the tunnel.

Cet1 triphosphatase activity is strictly dependent on a divalent cation cofactor. The hydrolysis of 5' triphosphate RNA termini is optimal in the presence of magnesium, whereas NTP hydrolysis specifically requires manganese or cobalt. The location of a metal-binding site on the enzyme was determined by X-ray diffraction of Cet1(241–539) crystals that had been soaked in manganese chloride [5]. Manganese is coordinated with octahedral geometry to the sulfate inside the tunnel, to the side chain carboxylates of three glutamates, and to two waters. The three glutamates that comprise the metal-binding site of fungal RNA triphosphatase are located in motifs A and C, which define the metal-dependent RNA triphosphatase family. Substitution of any one of the three glutamates by alanine or glutamine inactivates Cet1. The motif A and C glutamates are also essential for the activities of vaccinia virus RNA triphosphatase, baculovirus RNA triphosphatase, *C. albicans* CaCet1, *S. pombe* Pct1, and *S. cerevisiae* Cth1. Thus, it is likely that motifs A and C comprise the metal binding site in all members of this enzyme family.

The structure of Cet1(241-539) with bound sulfate and manganese is construed to reflect that of the product complex of enzyme with the hydrolyzed γ phosphate [5]. The structure suggests a catalytic mechanism whereby acidic side chains located on the floor of the tunnel coordinate an essential divalent cation that in turn coordinates the γ phosphate. The metal ion would activate the γ phosphorus for direct attack by water and stabilize a pentacoordinate phosphorane transition state in which the attacking water is apical to the β phosphate leaving group. Interactions between the sulfate and basic side chains located on the walls of the tunnel would contribute to the coordination of the 5' phosphates in the ground state and the stabilization of the negative charge on the γ phosphate developed in the transition state. A key mechanistic distinction between the fungal-type RNA triphosphatases and the metazoan-type RNA triphosphatases is that the fungal-type enzymes do not form a covalent phosphoenzyme intermediate.

The prior art is deficient in the lack of methods that teach a person having ordinary skill in this art how to screen for a compound that inhibits cap formation by the enzymes of unicellular eukaryotic parasites such as Plasmodia. The prior art is also deficient in an identification and characterization of the enzymes comprising the mRNA capping apparatus of Plasmodia. In particular, the RNA triphosphatase component of the mRNA capping apparatus has not been identified and characterized in any unicellular eukaryotic parasite. The biochemical properties of an RNA triphosphatase from a unicellular eukaryotic parasite are not known. Hence, a mechanistic and structural comparison between the RNA triphosphatase of the parasite and the RNA triphosphatase of the metazoan host organism, which could underscore the potential of RNA triphosphatase as a therapeutic target for parasitic infections, is not possible. The present invention fulfills this longstanding need in the art.

SUMMARY OF THE INVENTION

The present invention facilitates the discovery of drugs that target an essential aspect of gene expression—the formation of the mRNA 5' cap m7GpppN—in unicellular eukaryotic parasites.

The invention discloses the amino acid sequences of the *Plasmodium falciparum* RNA triphosphatase and RNA guanylyltransferase, which catalyze the first and second steps of mRNA cap formation, respectively. The invention also provides for expression vectors and recombinant *Plasmodium falciparum* RNA triphosphatase and RNA guanylyltransferase.

The invention further encompasses in vitro screening methods to identify candidate inhibitors of the catalytic activity of RNA guanylyltransferase or the RNA 5' triphosphatase of unicellular eukaryotic parasites. These methods are simple, quantitative, and adaptable to calorimetric, spectrophotometric, or fluorescence detection assays that are suited to high-throughput screening for inhibitors of the RNA triphosphatase of Plasmodia and other unicellular eukaryotic parasites.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the signature motifs of cellular and viral RNA guanylyltransferases. Six collinear sequence elements, designated motifs I, III, IIIa IV, V, and VI, are present in metazoan, plant, and viral capping enzymes. The amino acid sequences are aligned for the guanylyltransferases of *S. cerevisiae* (Sce), *S. pombe* (Spo), *C. albicans* (Cal), Chlorella virus PBCV-1 (ChV), *Caenorhabditis elegans* (Cel) mouse (Mus), *Drosophila melanogaster* (Dme), *Xenopus laevis* (Xle), *Arabidopsis thaliana* (Ath), *Trypanosoma brucei* gambiense (Tbr), *Crithidia fasciculata* (Cfa), African swine fever virus (ASF), and AcNPV baculovirus (AcNPV). The motifs of the *Plasmodium falciparum* (Pfa) guanylyltransferase are listed below the other aligned sequences. The numbers of amino acid residues separating the motifs are indicated. The amino acids of the Sce enzyme that are essential for its function in vivo are denoted by dots. Specific contacts between amino acid side chains and the GTP substrate in the ChV capping enzyme-GTP cocrystal are indicated by arrowheads.

FIG. 4 shows the amino acid sequence of the *Plasmodium falciparum* RNA guanylyltransferase Pgt1. The six nucleotidyl transferase motifs in the guanylyltransferase are highlighted in shaded boxes.

FIG. 5 shows the purification and guanylyltransferase activity of *Plasmodium falciparum* Pgt1.

FIG. 6 show the dependence of guanylyltransferase activity on enzyme concentration and divalent cation concentration.

FIG. 10 shows the amino acid sequence of *Plasmodium falciparum* RNA triphosphatase Prt1. The phosphohydrolase motifs A, B and C are highlighted in shaded boxes. The C-terminus of the truncated Prt1-CΔ140 polypeptide is indicated by the dot above the sequence.

FIG. 11 shows the purification and metal-dependent phosphohydrolase activity of *P. falciparum* RNA triphosphatase.

FIG. 12 shows the ATPase and RNA triphosphatase activities of *P. falciparum* Prt1.

DETAILED DESCRIPTION OF THE INVENTION

Figure 2:
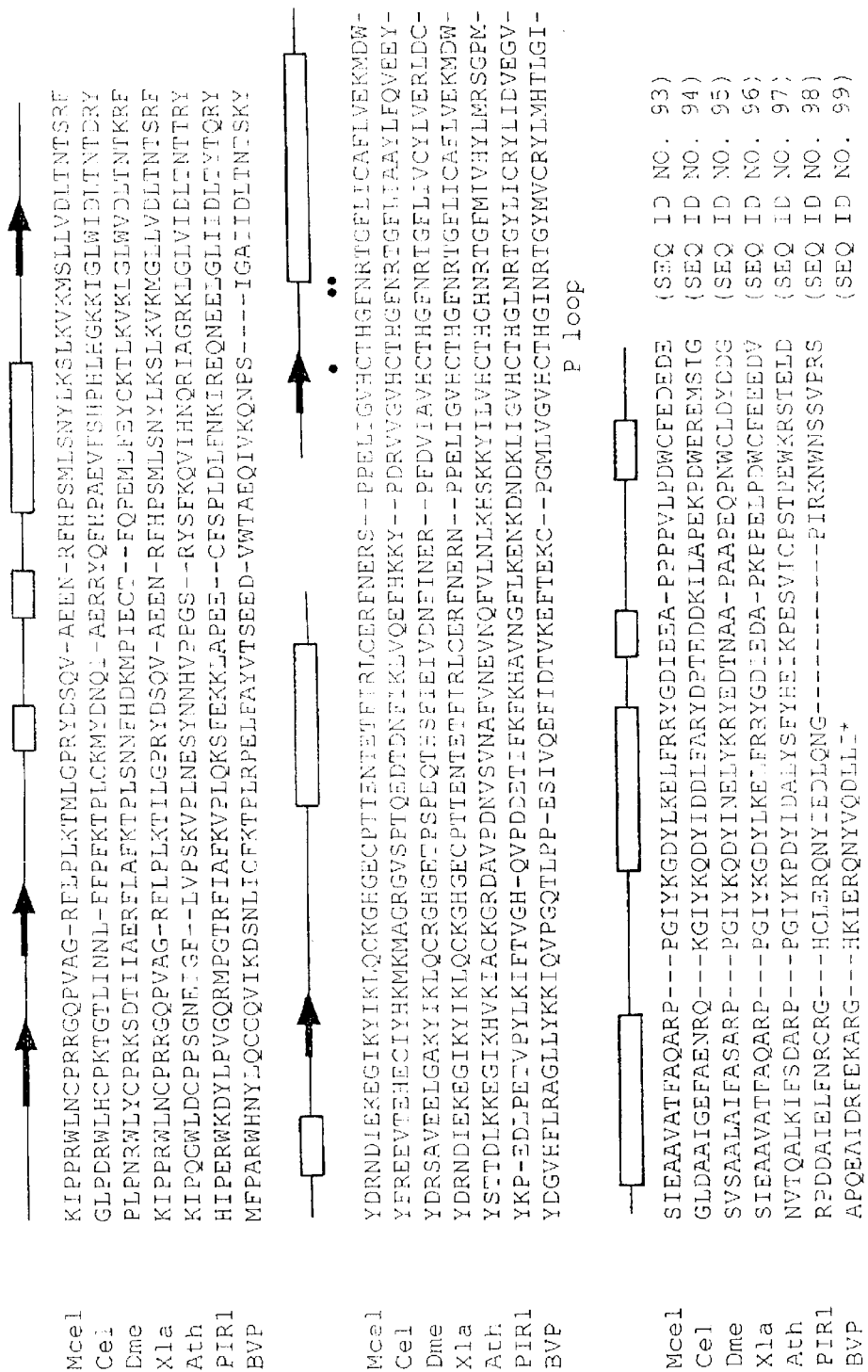
FIG. 2 shows an amino acid sequence alignment of the RNA triphosphatase domain of mammalian capping enzyme (Mce1) with other metazoan RNA capping enzymes from *Xenopus laevis* (Xla), *Drosophila melanogaster* (Dme), *C. elegans* (Cel), and *Arabidopsis thaliana* (Ath) and related RNA-specific 5' phosphatases BVP and PIR1. Structural elements of the Mce1 RNA triphosphatase are shown at the top with α helices depicted as boxes and β strands as arrows. The P loop containing the active site cysteine nucleophile is highlighted in the shaded box. Amino acids within the P loop that are essential for the RNA triphosphatase activity of Mce1 are denoted by dots above the sequence.

The present invention is directed to the identification of compounds that inhibits the growth of *Plasmodium falciparum* and other unicellular eukaryotic parasites by virtue of the effects of said compounds on the capping of parasite mRNA.

The present invention provides isolated DNAs encoding a RNA guanylyltransferase and a RNA 5' triphosphatase from *Plasmodium falciparum*, vectors for expression of recombinant RNA guanylyltransferase and RNA 5' triphosphatase, and purified RNA guanylyltransferase and RNA 5' triphosphatase having amino acid sequences of SEQ ID No. 1 and 2 respectively.

It is well known in the art that the amino acid sequence of a protein is determined by the nucleotide sequence of the DNA that encodes the protein. Because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention also encompass those degenerate sequences that encode the polypeptides of the subject invention, or a fragment or variant thereof. Accordingly, any nucleotide sequence (mutated from the sequences disclosed herein) which encodes the mRNA capping enzymes described herein comes within the scope of this invention and the claims appended hereto.

Also, as described herein, fragments or mutated versions of the mRNA capping enzymes are an aspect of the subject invention so long as such fragments or mutated versions retain the biochemical activity so that such fragments or mutated versions are useful in the methods described herein. As used herein, "fragment," as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. As used herein, "mutated version," as applied to a polypeptide, will ordinarily be an altered form of the polypeptide in which one or more amino acids are substituted by different amino acids or by modified amino acids. Mutated versions can be generated by methods known to those skilled in the art, e.g., by chemical modification of naturally occurring or recombinant protein, by recombinant DNA techniques using an expression vector that encodes a defined fragment, or by chemical synthesis. The ability of a candidate fragment or mutated version to exhibit a characteristic of the mRNA capping enzymes can be readily assessed by a person having ordinary skill in this art by using the methods described herein.

In one embodiment of the present invention, there is provided a method of screening for a compound that inhibits the catalytic activity of Plasmodium RNA guanylyltransferase, comprising the steps of: a) contacting said Plasmodium RNA guanylyltransferase with guanosine triphosphate and a divalent cation cofactor in the presence or absence of a test compound; and detecting formation of a covalent enzyme-GMP intermediate. A lack of formation of an enzyme-GMP intermediate or a reduction in the formation of said intermediate indicates inhibition of said Plasmodium RNA guanylyltransferase by said test compound. Preferably, the divalent cation cofactor is manganese or magnesium. Detection of an enzyme-GMP intermediate may be by any method readily known to those having ordinary skill in this art; preferable methods include radioisotope assay and fluorescence assay. A representative Plasmodium RNA guanylyltransferase is the RNA guanylyltransferase from *Plasmodium falciparum* disclosed herein.

In another embodiment of the present invention, there is provided a method of screening for a compound that inhibits the catalytic activity of Plasmodium RNA guanylyltransferase, comprising the steps of: a) contacting said Plasmodium RNA guanylyltransferase with guanosine triphosphate and a divalent cation cofactor and a diphosphate-terminated RNA in the presence or absence of a test compound; and detecting formation of a GMP-capped RNA. A lack of formation of a GMP-capped RNA or a reduction in the formation of said GMP-capped RNA indicates inhibition of said Plasmodium RNA guanylyltransferase by said test compound. Preferably, the divalent cation cofactor is manganese or magnesium. Although detection of a GMP-capped RNA may be by any method readily known to those having ordinary skill in this art, preferable methods include radioisotope assay and fluorescence assay. A representative Plasmodium RNA guanylyltransferase is the RNA guanylyltransferase from *Plasmodium falciparum* disclosed herein, i.e., Plasmodium guanylyltransferase has the amino acid sequence of SEQ ID No. 1, is a fragment of the guanylyltransferase with the amino acid sequence of SEQ ID No. 1, or is a mutated version of the guanylyltransferase with the amino acid sequence of SEQ ID No. 1.

In yet another embodiment of the present invention, there is provided a method of screening for a compound that inhibits the catalytic activity of unicellular eukaryotic parasite RNA 5' triphosphatase, comprising the steps of: a) contacting said parasite RNA 5' triphosphatase with a 5' triphosphate-terminated RNA or a nucleoside triphosphate and a divalent cation cofactor in the presence or absence of a test compound; and detecting hydrolysis of said 5' triphosphate-terminated RNA or nucleoside triphosphate. A lack of hydrolysis of said 5' triphosphate-terminated RNA or nucleoside triphosphate or a reduction in the hydrolysis of said 5' triphosplhate-terminated RNA or nucleoside triphosphate indicates inhibition of said parasite RNA 5' triphosphatase by said test compound. Preferably the divalent cation cofactor is magnesium, manganese or cobalt. Although detection of hydrolysis may be by any method readily known to those having ordinary skill in this art, preferable methods include radioisotope assay, calorimetric assay, spectrophotometric assay, and fluorescence assay. A representative parasite RNA triphosphatase is the RNA triphosphatase from *Plasmodium falciparum* disclosed herein.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. A coding sequence is "operably linked" and "under the control" of transcriptional and translational control sequences in a cell when RNA polymerase transcribes the coding sequence into mRNA, which is then translated into the protein encoded by the coding sequence. The transformed hosts can be fermented and cultured according to means known in the art to achieve optimal cell growth.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host organism" is meant to include not only prokaryotes but also eukaryotes such as yeast, plant, protozoan, and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells, insect cells, and plant cells, such as *Arabidopsis thaliana* and *Tobaccum nicotiana*.

The following examples are given for the purpose of illustrating various embodiments of the invention and are not meant to limit the present invention in any fashion:

EXAMPLE 1
Identification of *Plasmodium falciparum* RNA Guanylyltransferase, Pgt1

A candidate *Plasmodium falciparum* mRNA guanylyltransferase was identified on phylogenetic grounds. The candidate enzyme is a 520 amino acid polypeptide encoded by a continuous ORF on chromosome 14 (FIG. 4). The signature features of mRNA guanylyltransferases are a ping-pong reaction mechanism of nucleotidyl transfer through a covalent enzyme-(lysyl-N)-GMP intermediate and a set of six conserved peptide motifs (I, III, IIIa, IV, V, and VI) involved in GTP-binding and catalysis. The Plasmodium guanylyltransferase (henceforth named Pgt1) contains all six catalytic motifs in the standard order and spacing (FIG. 2 and FIG. 4), except that the 218-aa interval between motifs IIIa and IV of Pgt1 is exceptionally long. This segment in Pgt1 consists of reiterative tracts of hydrophilic amino acids and has no counterpart in other capping enzymes. The hydrophilic segment is predicted, based on the crystal structure of Chlorella virus guanylyltransferase [9], to comprise a large surface loop. All of the amino acids within the six motifs that are essential for the function of *S. cerevisiae* RNA guanylyltransferase Ceg1 [10] are conserved in the Plasmodium protein, as are the residue that make direct contact with the GTP substrate in the Chlorella virus guanylyltransferase-GTP cocrystal (FIG. 1).

EXAMPLE 2
Pgt1 Expression Vector

A DNA fragment containing the PGT1 open reading frame was amplified by polymerase chain reaction from total *P. falciparum* genomic DNA using oligonucleotide primers designed to introduce an NdeI restriction site at the predicted translation start codon and a XhoI site 3' of the predicted stop codon. The 1.6-kbp PCR product was digested with NdeI and XhoI and inserted into the T7 RNA polymerase-based expression plasmid pET16b to generate plasmid pET-His-Pgt1. The nucleotide sequence of the Plasmodium DNA insert was determined. The predicted amino acid sequence of the 520-amino acid Pgt1 protein encoded by this plasmid is shown in FIG. 4.

EXAMPLE 3
Production and Purification of Pgt1

Pgt1 protein was produced in bacteria as an N-terminal His$_{10}$-tagged fusion protein. pET-His-Pgt1 was transformed into *Escherichia coli* BL21-CodonPlus(DE3). A 500-ml culture of *E. coli* BL21-CodonPlus(DE3)/pET-His-Pgt1 was grown at 37° C. in Luria-Bertani medium containing 0.1 mg/ml ampicillin and 50 µg/ml chloramphenicol until the A$_{600}$ reached 0.5. The culture was adjusted to 2% ethanol and then incubated at 17° C. for 24 h. Cells were harvested by centrifugation and the pellet was stored at −80° C. All subsequent procedures were performed at 4° C. Thawed bacteria were resuspended in 50 ml of buffer A (50 mM Tris HCl [pH 7.5], 0.25 M NaCl, 10% sucrose). Cell lysis was achieved by addition of lysozyme and Triton X-100 to final concentrations of 100 µg/ml and 0.1%, respectively. The lysate was sonicated to reduce viscosity and insoluble material was removed by centrifugation for 45 min at 17,000 rpm in a Sorvall SS34 rotor.

Figure 5A:
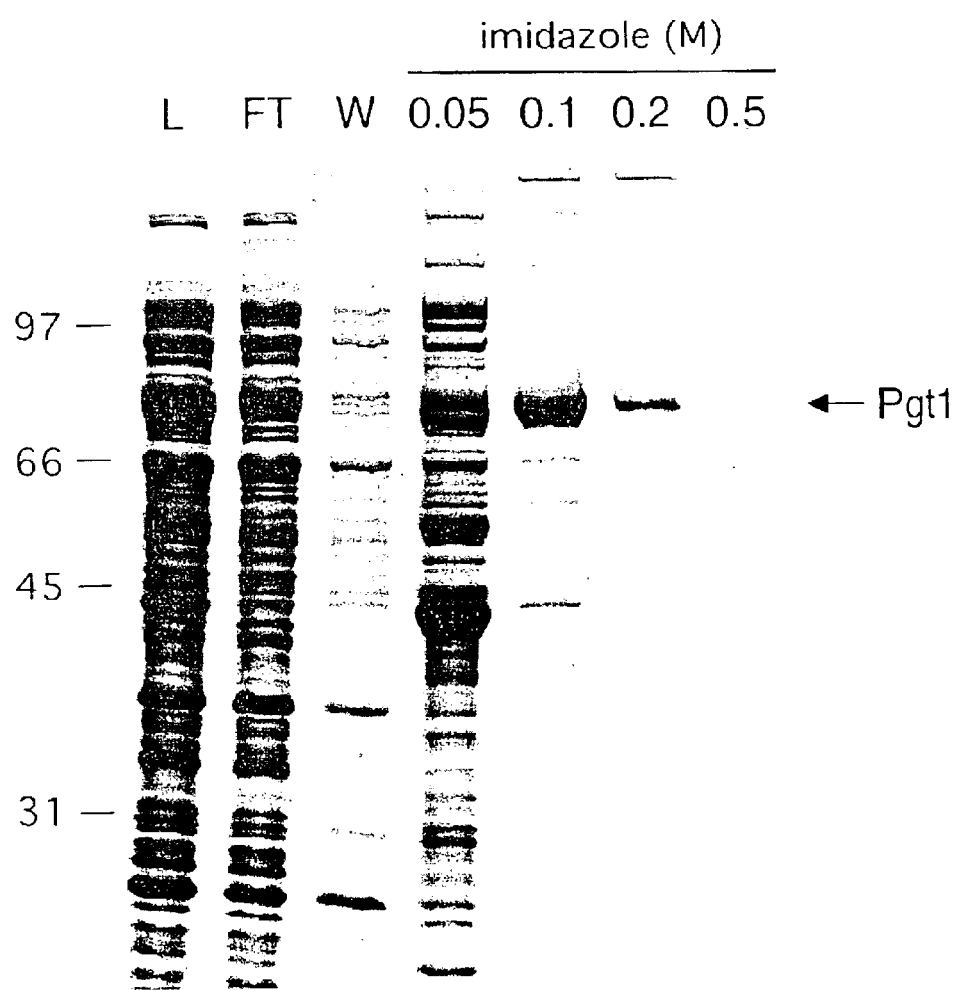
FIG. 5A shows Pgt1 purification. Aliquots (15 μl) of the soluble bacterial lysate (L) Ni-agarose flow-through (FT), wash (W) and the indicated imidazole eluates were analyzed by SDS-PAGE. The fixed gel was stained with Coomassie blue dye. The positions and sizes (in kDa) of marker polypeptides are shown on the left.

The His-tag allowed for rapid enrichment of Pgt1 based on the affinity of the tag for immobilized nickel (FIG. 5A). The soluble extract was applied to a 5-ml column of Ni-NTA-agarose resin (Qiagen) that had been equilibrated with buffer A containing 0.1% Triton X-100. The column was washed with 25 ml of the same buffer and then eluted step-wise with 12.5-ml aliquots of buffer B (50 mM Tris-HCl [pH 8.0], 0.25 M NaCl, 10% glycerol, 0.05% Triton X-100) containing 0.05, 0.1, 0.2, 0.5, and 1 M imidazole. The polypeptide compositions of the column fractions were monitored by SDS-polyacrylamide gel electrophoresis (PAGE). The 70 kDa recombinant Pgt1 polypeptide was retained on the column and recovered predominantly in the 0.1 M imidazole fraction (which contained 5 mg of protein). The enzyme preparation was stored at −80° C.

EXAMPLE 4
Demonstration and Characterization of the Guanylyltransferase Activity of Pgt1

Figure 5B:
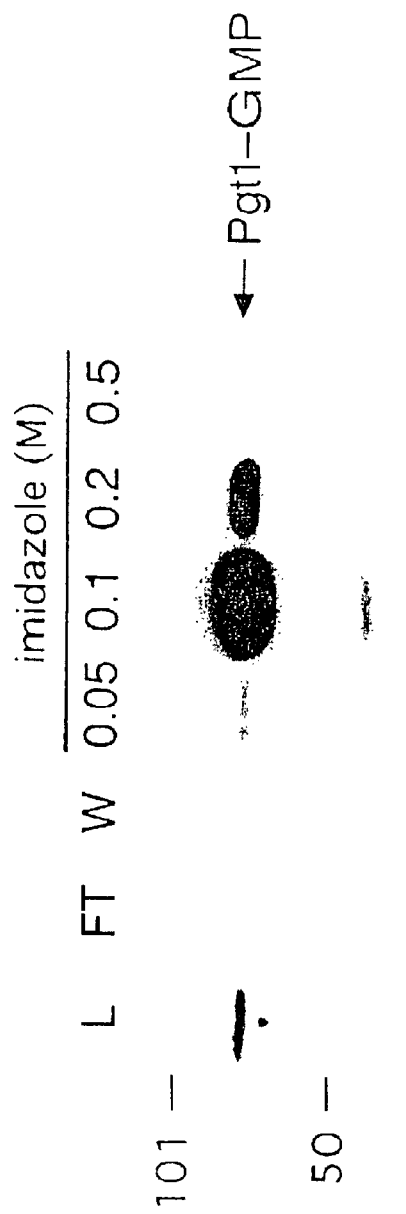
FIG. 5B shows guanylyltransferase activity of Pgt1. Reaction mixtures (20 μl) containing 50 mM Tris-HCl (pH 8.0), 5 mM DTT, 5 mM $MgCl_2$, 0.17 μM [$\alpha^{32}$P]GTP, and 1 μl of the protein fractions specified above the lanes were incubated at 30° C. for 10 min. The reaction products were resolved by SDS-PAGE. An autoradiograph of the dried gel is shown. The positions and sizes (in kDa) of marker polypeptides are indicated on the left.
Figure 6A:
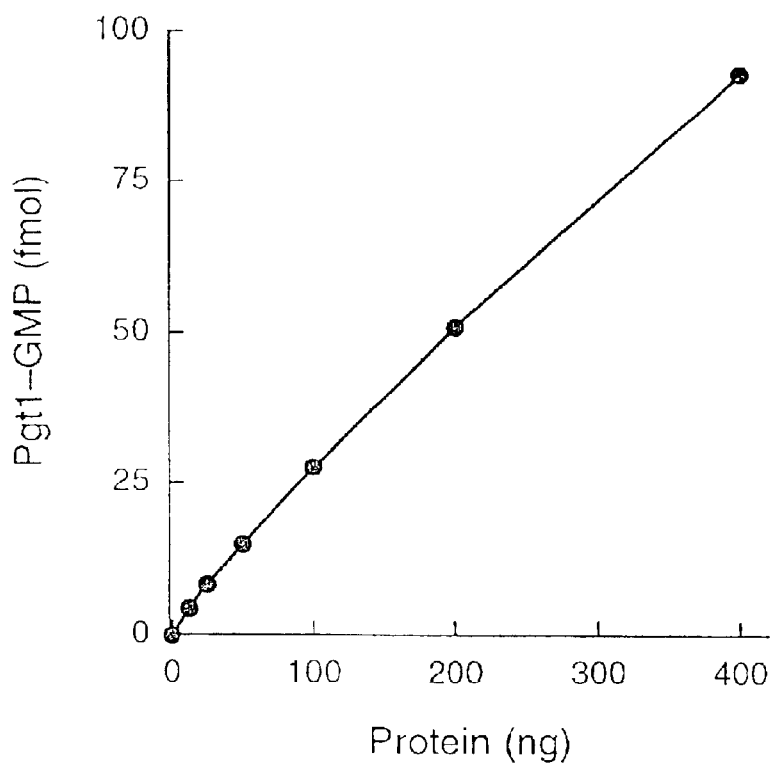
FIG. 6A shows protein titration. Reaction mixtures (20 μl) containing 50 mM Tris HCl (pH 8.0), 5 mM DTT, 5 mM $MgCl_2$, 0.17 μM [$\alpha^{32}$ P]GTP, and Pgt1 as specified were incubated at 30° C. for 10 min. The reaction was quenched with SDS and the products were resolved by SDS-PAGE. The extent of Pgt1-[$^{32}$P]GMP formation was quantitated by scanning the gel with a Fujix Phosphorimager and is plotted as a function of input protein.
Figure 6B:
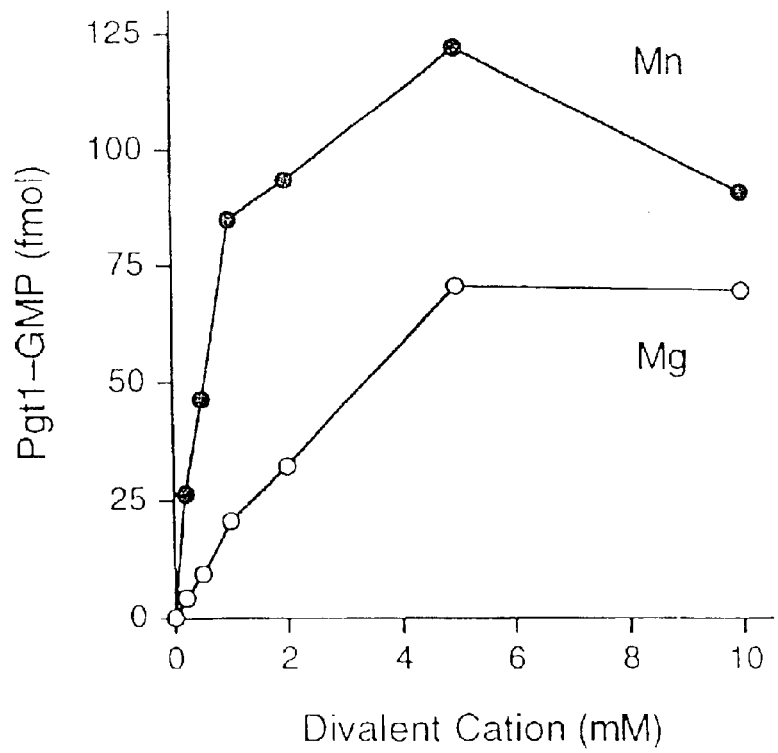
FIG. 6B shows divalent cation requirement. Reaction mixtures (20 μl) containing 50 mM Tris HCl (pH 8.0), 5 mM DTT, 0.17 μM [$\alpha^{32}$ P]GTP, 200 ng of Pgt1, and either $MgCl_2$ or $MnCl_2$ as specified were incubated at 30° C. for 10 min. The extent of Pgt1-[$^{32}$P]GMP formation is plotted as a function of divalent cation concentration.

Guanylyltransferase activity was measured by reaction of the protein with [$\alpha^{32}$P]GTP in the presence of a divalent cation to form the covalent enzyme-GMP intermediate (FIG. 5B). Enzyme-guanylate formation was linear with respect to Pgt1 concentration (FIG. 6A) and was strictly dependent on a divalent cation cofactor—either manganese or magnesium (FIG. 6B). Other divalent cations—calcium, cobalt, copper and zinc—did not support guanylyltransferase activity (data not shown).

Figure 7:
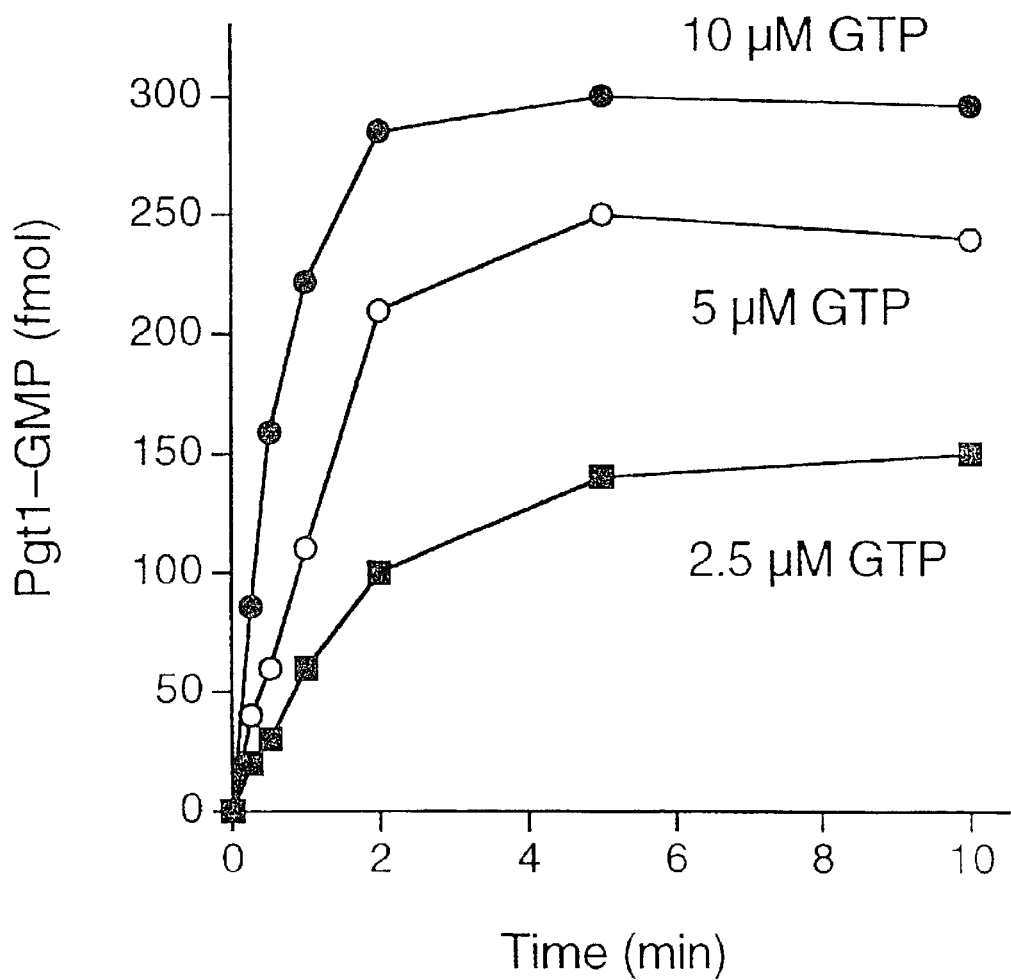
FIG. 7 shows a kinetic analysis of Pgt1-GMP formation. Reaction mixtures (100 μl) containing 50 mM Tris HCl (pH 8.0), 5 mM DTT, 5 mM MnCl$_2$, 1 µg of Pat1, and either 2.5, 5, or 10 µM [α$^{32}$P]GTP were incubated at 30° C. The reaction was initiated by adding Pgt1. Aliquots (10 µl) were withdrawn at the times indicated and quenched immediately with SDS. Pgt1-[$^{32}$P]GMP formation is plotted as a function of time.

Pgt1 formed a covalent intermediate with [$\alpha^{32}$P]GTP but was unable to do so with [$\alpha^{32}$P]ATP (not shown). The rate and extent of formation of the covalent intermediate was proportional to GTP concentration and leveled off at $\geq 10$ µM GTP (FIG. 7 and data not shown). Approximately 20% of the input enzyme molecules were labeled with GMP during the reaction with 10 µM GTP and 5 mM MnCl$_2$. The reaction with 10 µM GTP displayed pseudo first-order kinetics with an apparent rate constant of 1.4 min$^{-1}$.

EXAMPLE 5
Native Size Of Pgt1

Figure 8:
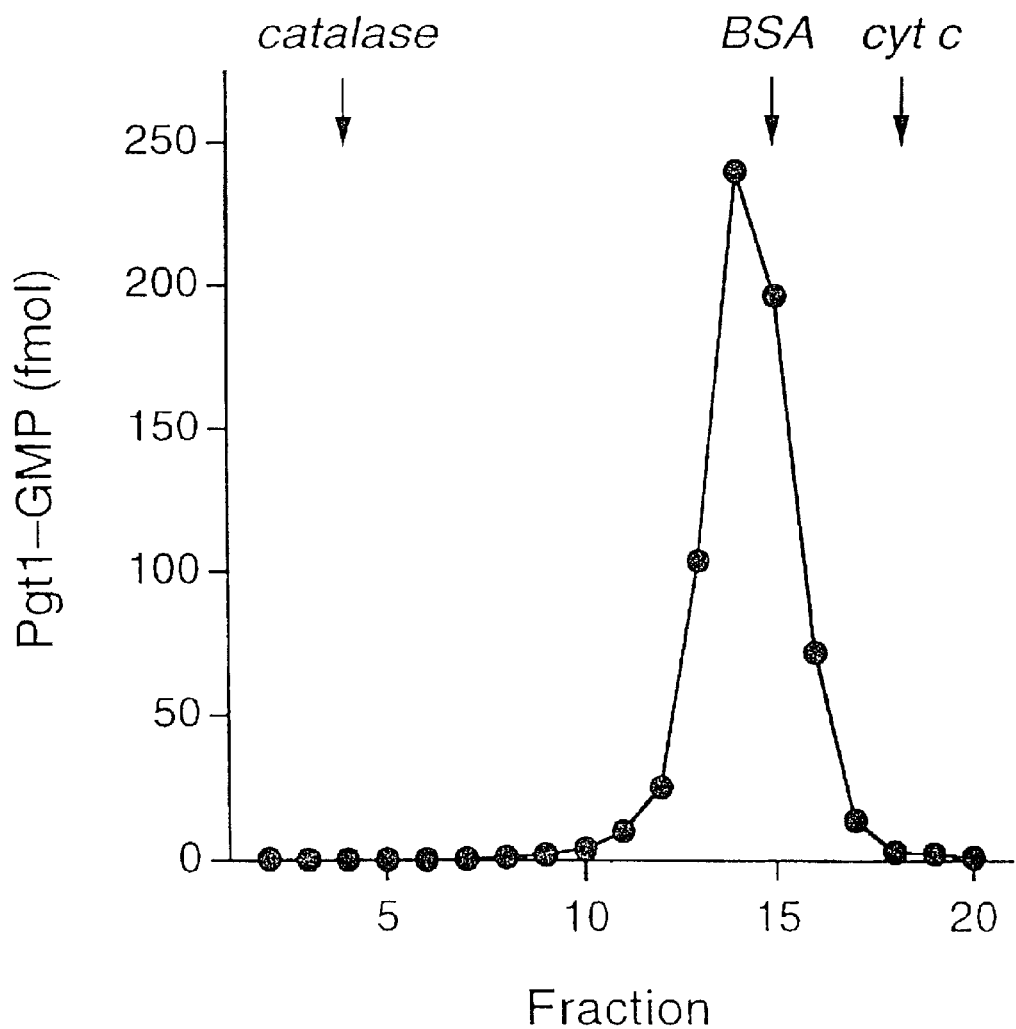
FIG. 8 shows glycerol gradient sedimentation of *P. falciparum* guanylyltransferase. An aliquot of the Ni-agarose fraction of Pgt1 (50 µg of protein) was mixed with marker proteins catalase (50 µl), BSA (50 µg), and cytochrome c (50 µg) and the mixture was applied to a 4.8-ml 15–30% glycerol gradient containing 0.5 M NaCl, 50 mM Tris-HCl (pH 8.0), 5 mM DTT, and 0.05% Triton X-100. The gradient was centrifuged at 50,000 rpm for 18 h at 4° C. in a Beckman SW50 rotor. Fractions (~0.23 ml) were collected from the bottom of the tube. The polypeptide compositions of the fractions were analyzed by SDS-PAGE. The peaks of the internal marker proteins are indicated by arrowheads. Aliquots (2 µl) of each fraction were assayed for enzyme-GMP formation in a reaction mixture (20 µl) containing 50 mM Tris-HCl (pH 8.0), 5 mM DTT, 5 mM MnCl$_2$, and 5 µM [α$^{32}$P]GTP.

The native size of Pgt1 was analyzed by glycerol gradient sedimentation with internal standards (FIG. 8). The guanylyltransferase activity sedimented as a single peak at 4.5 S, which suggested that Pgt1 is a monomer in solution. The activity profile coincided with the distribution of the Pgt1 polypeptide (not shown).

EXAMPLE 6
Pgt1 Catalyzes Capping of RNA

Figure 9:
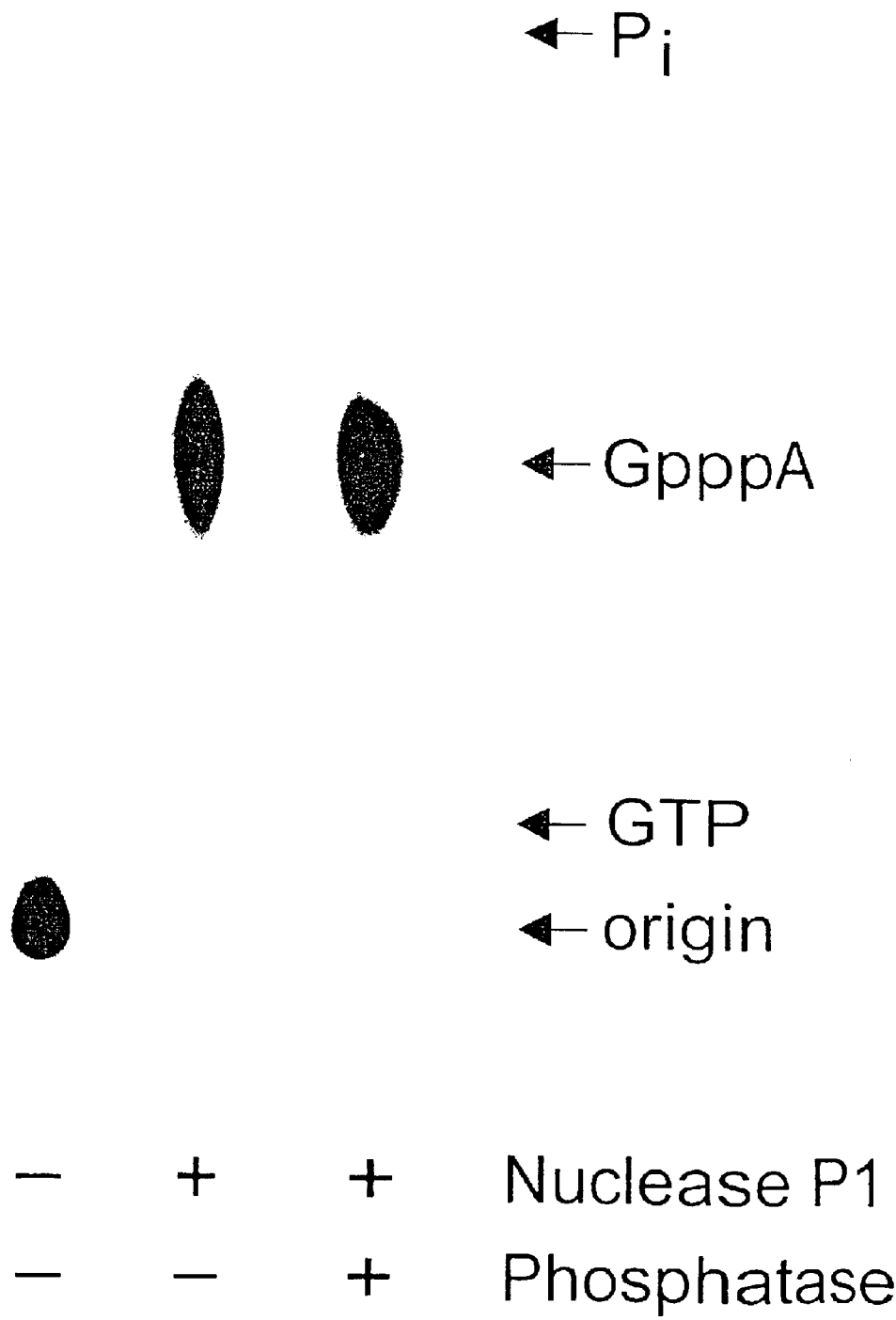
FIG. 9 shows the RNA capping activity of recombinant Pgt1. The isolated Pgt1-[$^{32}$P]GMP complex was reacted with 5' diphosphate-terminated poly(A) and the RNA reaction product was deproteinized and then recovered by ethanol-precipitation. Aliquots of the product were treated with nuclease P1 followed by treatment with alkaline phosphatase. The treated samples and an undigested control sample of the reaction product were analyzed by thin-layer chromatography on polyethyleneimine-cellulose plates developed with 0.45 M ammonium sulfate. An autoradiograph of the chromatogram is shown. The chromatographic origin and the positions of GpppA, GTP, and P$_i$ are indicated on the right.

That Pgt1 is a bona fide capping enzyme was demonstrated by isolating the Pgt1-[$^{32}$P]GMP intermediate by gel filtration and demonstrating that it catalyzed transfer of the GMP to diphosphate-terminated poly(A) to form a GpppA cap structure (FIG. 9).

To form the Pgt1-[$^{32}$P]GMP intermediate, a reaction mixture (100 µl) containing 50 mM Tris HCl (pH 8.0), 5 mM DTT, 2.5 mM MgCl$_2$, 5 µM [$\alpha^{32}$P]GTP, and 10 µg of Pgt1 was incubated for 30 min at 30° C. The mixture was adjusted to 25 mM EDTA and 10% glycerol. The native Pgt1-[$^{32}$P]GMP complex was resolved from free [$\alpha^{32}$P]GTP by gel filtration through a 1-ml column of Sephadex G-50 that had been equilibrated with buffer containing 50 mM Tris-HCl (pH 8.0), 50 mM NaCl, 5 mM DTT, 10% glycerol, 0.05% Triton X-100. Gel filtration was performed at 4 ° C. Five-drop fractions (~180 µl) were collected serially and the $^{32}$P elution profile was determined by Cerenkov counting of each fraction.

An aliquot (25 μl) of the gel-filtered Pgt1-[$^{32}$P]GMP complex (recovered in the void volume of the G-50 column) was incubated for 30 min at 30° C. in a reaction mixture (100 μl) containing 50 mM Tris HCl (pH 8.0), 2 mM MgCl$_2$, 5 mM, DTT, and 75 pmol of 5' diphosphate-terminated poly (A). The reaction products were then extracted once with phenol and once with chloroform-isoamyl alcohol (24:1). RNA was recovered from the aqueous phase by ethanol-precipitation and resuspended in 20 μl of 10 mM Tris HCl (pH 8.0), 1 mM EDTA. Aliquots (4 μl) were digested with 5 μg of nuclease P1 for 60 min at 37° C. followed by digestion with 1 unit of calf intestine alkaline phosphatase for 60 mill at 37° C. The digests were analyzed by thin-layer chromatography on polyethyleneimine-cellulose plates developed with 0.45 M ammonium sulfate. The radiolabeled material was visualized by autoradiography.

The TLC analysis showed that the isolated Pgt1-[$^{32}$P] GMP intermediate transferred the GMP to diphosphate-terminated poly(A) to form a radiolabeled GpppA cap structure that was liberated from the RNA by digestion with nuclease P1 and was resistant to alkaline phosphatase (FIG. 9).

EXAMPLE 7

The Monofunctional Plasmodium mRNA Guanylyltransferase is Structurally Distinct From the Bifunctional Metazoan Capping Enzyme Motif I of Pgt1 (62-KxDGxR-67) contains the lysine nucleophile to which GMP becomes covalently attached during the guanylyltransferase reaction. The position of Lys62 relative to the N-terminus of Pgt1 is typical of the monofunctional guanylyltransferases of fungi and Chlorella virus (where the motif I lysine is located at positions 70, 67, 67, and 84 in the *S. cerevisiae, S. pombe, C. albicans*, and Chlorella virus enzymes, respectively). The Plasmodium enzyme conspicuously lacks the ~200-aa N-terminal RNA triphosphatase domain present in metazoan and higher plant capping enzymes. Metazoan RNA triphosphatases belong to a distinct branch of the cysteine phosphatase enzyme superfamily and they are easily identified by their primary structure. No ORF encoding a homolog of the metazoan RNA triphosphatase was found upstream of the PGT1 gene on the *P. falciparum* chromosome 14 contig, nor was such an ORF found elsewhere in the *P. falciparum* genome database at NCBI. Thus, Plasmodium apparently does not encode a metazoan-type mRNA capping enzyme.

EXAMPLE 8

*Plasmodium falciparum* Encodes a Fungal-type RNA Triphosphatase, Prt1

The similarities between the Plasmodium and fungal guanylyltransferases, and the apparent absence of a metazoan-type RNA triphosphatase in Plasmodium, suggested that *P. falciparum* might possess a fungal-type RNA triphosphatase.

Figure 3:
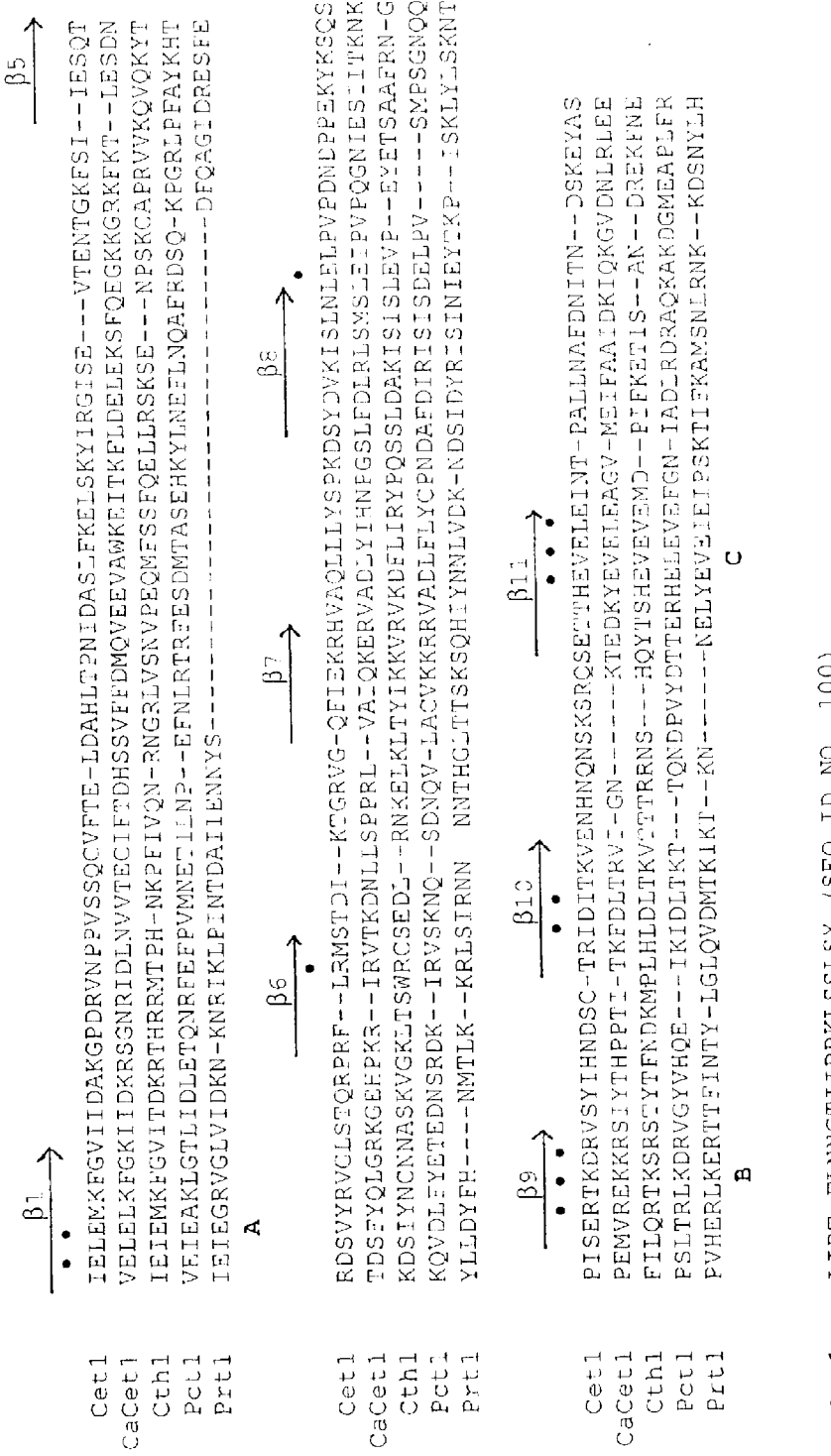
FIG. 3 shows structural conservation among fungal RNA triphosphatases. The amino acid sequences of the catalytic domains of fungal RNA triphosphatases *S. cerevisiae* Cet1, *C. albicans* CaCet1, *S. cerevisiae* Cth1, and *S. pombe* Pct1 are aligned. Gaps in the alignment are indicated by dashes. The β strands that form the triphosphate tunnel of Cet1 are denoted above the sequence. Hydrophilic amino acids that comprise the active site within the tunnel are denoted by dots. Conserved motifs A (β1), B (β9) and C (β11) that define the metal-dependent RNA triphosphatase family are indicated below the sequence. The amino acid sequence of *P. falciparum* Prt1 is aligned to those of the four fungal triphosphatases. Peptide segments with the highest degree of conservation in all five proteins are highlighted by the shaded boxes. The poly-asparagine insert in Prt1 is omitted from the alignment and is denoted by a triangle under the sequence between strands β6 and β7.

The *S. cerevisiae* RNA triphosphatase Cet1 exemplifies a growing family of metal-dependent phosphohydrolases that includes the RNA triphosphatases encoded by other fungi (*Candida albicans* and *Schizosaccharomyces pombe*), by algal virus PBCV-1, and by several groups of animal viruses (poxviruses, African swine fever virus, and baculoviruses). The yeast/viral triphosphatase family is defined by two glutamate-rich peptide motifs (motifs A and C) that are essential for catalytic activity and comprise the metal binding site and by a basic peptide motif (motif B) that is implicated in binding the 5' triphosphate moiety of the substrate (FIG. 3). The crystal structure of *S. cerevisiae* RNA triphosphatase reveals that the active site is located within the hydrophilic core of a topologically closed 8-stranded β barrel—the so-called "triphosphate tunnel". The β strands comprising the tunnel (β1, β5, β6, β7, β8, β9, β10, and β11) are displayed over the Cet1 amino acid sequence shown in FIG. 3.

A PSI-BLAST search [18] initially identified a short segment of weak similarity between Cet1 and the hypothetical *P. falciparum* protein PFC0985c encoded on chromosome 3 (BLAST score 42). The similarity between PFC0985c and the other fungal RNA triphosphatases was statistically significant after the first iteration of the search (BLAST score 122).

A DNA fragment containing the ORF was amplified by polymerase chain reaction from total *P. falciparum* genomic DNA using oligonucleotide primers designed to introduce an NcoI restriction site at the methionine codon and a BamHI site 3' of the predicted stop codon. The PCR product was digested with NcoI and BamHI and cloned into plasmid pYX132. The nucleotide sequence of the Plasmodium DNA insert was determined. The predicted amino acid sequence of the 596-amino acid putative Plasmodium RNA triphosphatase (henceforth named Prt1) is shown in FIG. 10.

The Plasmodium and fungal protein sequences were then aligned manually using the tertiary structure of Cet1 and known structure-activity relationships for fungal RNA triphosphatases as a guide. It was thereby possible to identify in the Plasmodium protein counterparts of all eight β strands of the Cet1 triphosphate tunnel (FIG. 3). The Plasmodium protein contains a 162-amino acid segment between strands β6 and β7, consisting mainly of poly-asparagine and acidic residues, that has no counterpart in other RNA triphosphatases (FIG. 10). Reference to the Cet1 structure suggests that this segment is a surface loop emanating from the roof of the tunnel. The instructive point is that the twelve catalytically important hydrophilic amino acids within the tunnel that comprise the active site of fungal RNA triphosphatases are conserved in the Plasmodium Prt1 protein (FIG. 3).

EXAMPLE 9

Demonstration and Characterization of the Triphosphatase Activity of Prt1

That Prt1 is a bona fide member of the fungal-type family of metal-dependent RNA triphosphatases was demonstrated by isolating and characterizing a catalytically active recombinant version of the protein.

A deletion mutant PRTI-CΔ140 lacking the C-terminal 140 amino acids was generated by PCR amplification with a primer designed to introduce a new stop codon and BamHI site immediately downstream. The C-terminus of the Prt1-CΔ140 polypeptide is indicated by the dot above the sequence in FIG. 10. The PCR product was digested with NcoI and BamHI, the 5' overhangs were filled in with DNA polymerase, and the DNA was inserted into the filled-in BamHI site of pET28-His/Smt3 so as to fuse the ORF in-frame to N-terminal His/Smt3. The expression vector was transformed into *Escherichia coli* BL21-CodonPlus(DE3). A 200-ml culture amplified from a single transformant was grown at 37° C. in Luria-Bertani medium containing 60 μg/ml kanamycin and 100 μg/ml chloramphenicol until the $A_{600}$ reached 0.5. The culture was adjusted to 2% ethanol and 0.4 mM IPTG and then incubated at 17° C. for 16 h. Cells were harvested by centrifugation. All subsequent procedures were performed at 4° C. Bacteria were resuspended in 10 ml of buffer A (50 mM Tris HCl [pH 7.5], 0.25 M NaCl, 10% sucrose). Cell lysis was achieved by addition of lysozyme and Triton X-100 to final concentrations of 100 μg/ml and 0.1%, respectively. The lysate was sonicated to reduce viscosity and insoluble material was removed by centrifugation for 40 min at 16,000 rpm in a Sorvall SS34 rotor.

Figure 11A:
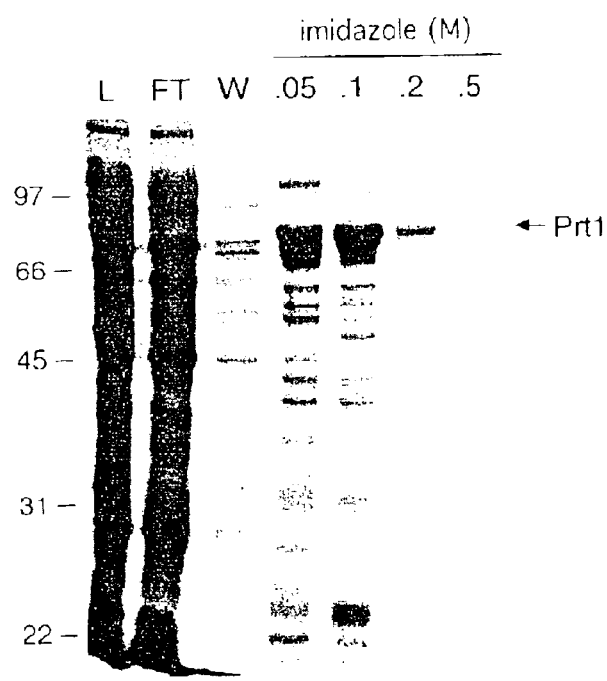
FIG. 11A shows Prt1 purification. Aliquots (15 µl) of the soluble bacterial lysate (L), the Ni-agarose flow-through (FT), wash (W), and indicated imidazole eluates were analyzed by SDS-PAGF. The fixed gel was stained with Coomassie brilliant blue dye.

The His$_6$-tag allowed for enrichment of Prt1 based on the affinity of the His/Smt3 leader for immobilized nickel (FIG. 11A). The soluble extract was applied to a 0.8-ml column of Ni-NTA-agarose resin (Qiagen) that had been equilibrated with buffer A containing 0.1% Triton X-100. The column was washed with 5 ml of the same buffer and then eluted step-wise with 1.5-ml aliquots of buffer (50 mM Tris-HCl [pH 8.0], 0.25 M NaCl, 10% glycerol, 0.05% Triton X-100) containing 0.05, 0.1, 0.2, and 0.5 M imidazole. The polypeptide compositions of the column fractions were monitored by SDS-polyacrylamide gel electrophoresis (PAGE). The recombinant Prt1 polypeptide was recovered predominantly in the 0.1 M imidazole fraction (which contained 0.9 mg of protein). The enzyme preparation was stored at −80° C.

Figure 11B:
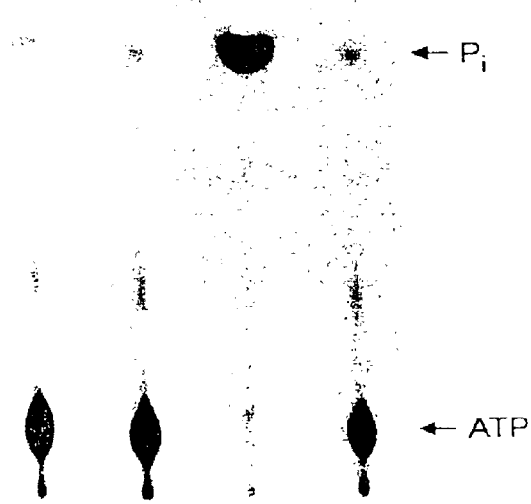
FIG. 11B shows manganese-dependent NTP hydrolysis. Phosphohydrolase reaction mixtures (10 µl) containing 50 mM Tris-HCl (pH 7.5), 5 mM DTT, 1 mM [γ$^{32}$P]ATP, 2 mM MnCl$_2$ or MgCl$_2$, and 0.6 µg of recombinant Prt1 (0.1 M imidazole eluate) were incubated for 15 min at 30° C. An aliquot (2.5 µl) of the reaction mixture was applied to a polyethyleneimine-cellulose TLC plate, which was developed 0.5 M LiCl, 1 M formic acid. The radiolabeled material was visualized by autoradiography. The positions of [γ$^{32}$P]ATP and $^{32}$P$_i$ are indicated.
Figures 12A, 12B:
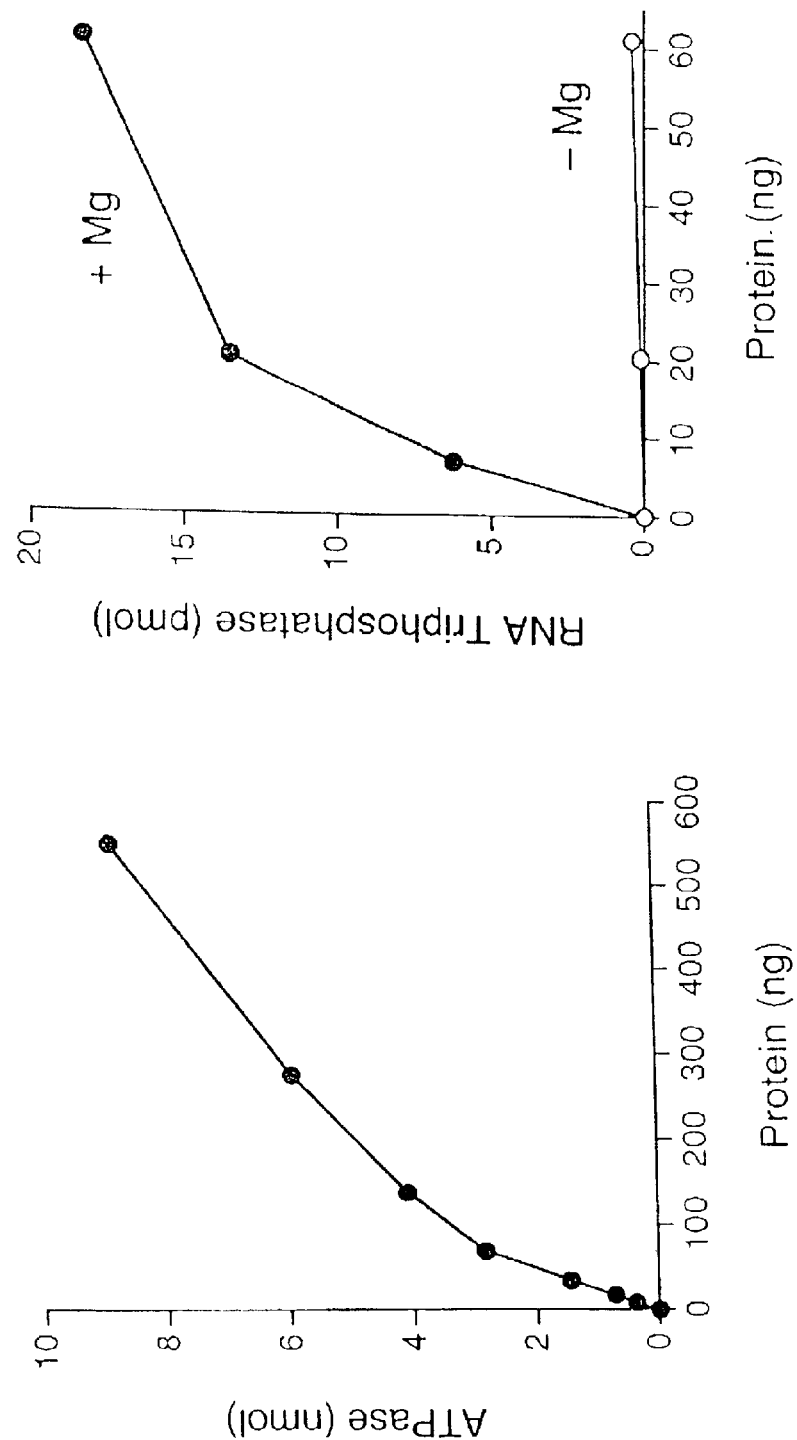
FIG. 12A shows dependence of ATPase activity on protein concentration. Reaction mixtures (10 µl) containing 50 mM Tris-HCl (pH 7.5), 5 mM DTT, 1 mM [γ$^{32}$P]ATP (10 nmol of ATP), 2 mM MnCl$_2$, and recombinant Prt1 as specified were incubated for 15 min at 30° C.
FIG. 12B shows magnesium-dependent RNA 5' triphosphatase activity. Reaction mixtures (10 µl) containing 50 mM Tris-HCl (pH 7.5), 5 mM DTT, 2 µM 5' [γ$^{32}$P]-labeled poly(A) (20 pmol of triphosplhate RNA ends), either 2 mM MgCl$_2$ or no added divalent cation, and recombinant Prt1 as specified were incubated for 15 min at 30° C. The reaction products were analyzed by TLC and the extent of $^{32}$P$_i$ formation was quantitated by scanning the chromatograms with a Phosphorimager. ATPase and RNA triphosphatase activities are plotted as a function of input protein.

Recombinant Prt1 displayed the signature biochemical feature of the fungal RNA triphosphatase family—it catalyzed the hydrolysis of the γ phosphate of ATP in the presence of manganese (FIG. 11B). Activity was dependent on a metal cofactor and, as with the fungal enzymes, magnesium was ineffective in supporting ATP hydrolysis by Prt1 (FIG. 11B). ATPase activity increased with increasing Prt1 concentration (FIG. 12A). Prt1 also catalyzed the metal-dependent hydrolysis of the γ phosphate of triphosphate-terminated RNA (FIG. 12B). Thus, Prt1 displays the requisite properties of a component of the Plasmodium mRNA capping apparatus.

EXAMPLE 10
Methods to Identify Inhibitors of Prt1

Prt1 is the newest member of the fungal/viral family of metal-dependent RNA triphosphatases defined by motifs A, B, and C. Prt1 is an extremely attractive antimalarial drug target because: (i) the active site structure and catalytic mechanism of this protein family are completely different from the RNA triphosphatase domain of the capping enzyme in humans and in arthropods and (ii) metazoans encode no identifiable homologs of the fungal or Plasmodium RNA triphosphatases. Thus, a mechanism-based inhibitor of Prt1 should be highly selective for the malaria parasite and have minimal effect on either the human host or the mosquito vector.

Given the central role of the mRNA cap in eukaryotic gene expression, an antimalarial drug that targets Prt1 would be effective at all stages of the parasite's life cycle. Also, the structural similarity between Prt1 and the fungal RNA triphosphatases raises the exciting possibility of achieving antifungal and antimalarial activity with a single class of mechanism-based inhibitors.

All members of this RNA triphosphatase family display magnesium dependent RNA triphosphatase activity. They also display robust nucleoside triphosphatase (NTPase) activity in the presence of manganese or cobalt as the divalent cation cofactor. Mutational analysis indicates that the NTPase function of the fungal/viral enzymes is performed by the same catalytic moieties on the enzyme that carry out the RNA triphosphatase reaction. Therefore, the measurement of either RNA triphosphatase or NTPase activity in vitro is a suitable means to screen for inhibitors of *Plasmodium falciparum* Prt1. However, assay of the NTP hydrolysis by Prt1 offers a much more convenient assay than RNA triphosphatase for conducting large scale testing of Prt1 inhibitors. This is because NTPs are commercially available (including radioactively labeled NTPs), whereas the synthesis of triphosphate-terminated RNA is technically complex.

Detection of NTP hydrolysis can entail the use of radio-labeled NTP and product analysis by thin layer chromatography (FIG. 11B). However, the assay is easily adapted to a non-radioactive calorimetric method of detection of $P_i$ release from NTP [19], a spectrophotometric assay for inorganic phosphate [20], or a fluorescence-based detection method [21, 22]. A colorimetric, spectrophotometric, or fluorescence-based assay of Prt1 activity is especially conducive to high-throughput screening of candidate inhibitors.

EXAMPLE 11
Heuristic Phylogeny of Eukaryotes Based on their Capping Enzymes

Capping enzymes are a good focal point for considering eukaryotic evolution because the mRNA cap structure is ubiquitous in eukaryotic organisms, but absent from the bacterial and archaeal kingdoms. Thus, any differences in the capping apparatus between taxa would reflect events that post-date the emergence of ancestral nucleated cells. The enzymes that catalyze the basic nucleic acid transactions (DNA replication, DNA repair, RNA synthesis, and RNA processing) are generally well conserved in lower and higher eukaryotes. Yet, in the case of the capping apparatus, there is a complete divergence of the triphosphatase component and of the physical linkage of the triphosphatase and guanylyltransferase in unicellular and multicellular organisms.

This suggests a heuristic scheme of eukaryotic phylogeny based on two features of the mRNA capping apparatus: the structure and mechanism of the triphosphatase component (metal-dependent "fungal" type versus metal-independent cysteine-phosphatase type) and whether the triphosphatase is physically linked in cis to the guanylyltransferase component. By these simple criteria relying on "black-and-white" differences in the same metabolic pathway, one arrives at different relationships among taxa than those suggested by comparisons of sequence variations among proteins that are themselves highly conserved in all eukaryotes [23]. For example, capping-based phylogeny would place metazoans in a common lineage with viridiplantae (exemplified by Arabidopsis) because all of these multicellular organisms have a cysteine-phosphatase type RNA triphosphatase fused in cis to their guanylyltransferase. Fungi and now Plasmodia (which are classified as Apicomplexa along with other pathogenic parasites Toxoplasma and Cryptosporidia) fall into a different lineage distinguished by a "Cet1-like" RNA triphosphatase that is physically separate from RNA guanylyltransferase. In contrast, the protein sequence variation-based scheme places fungi in the same supergroup as metazoa and puts the Apicomplexa nearer to plants. Assuming that multicellular organisms evolved from unicellular ancestors, it can be envisioned that a gene rearrangement event early in eukaryotic evolution transferred a cysteine-phosphatase domain into the same transcription unit as the guanylyltransferase, leading to creation of the triphosphatase-guanylyltransferase fusion protein that is seen today in multicellular eukaryotes. The fusion presumably allowed for the loss of a Cet1-like enzyme from the early metazoan/plant genome or else the divergence of such a protein to a point that it is no longer discernable as Cet1-like. The alternative (and perhaps less parsimonious) explanation that adheres to the sequence-based scheme would be that plants and metazoans independently experienced this gene fusion in distant branches of the phylogenetic tree.

It is conceivable that, as more eukaryotic genomes are sequenced, some species will be found to encode a Cet1-like triphosphatase fused to a guanylyltransferase, whereas others may encode a cysteine-phosphatase-type RNA triphosphatase that participates in cap formation but is separate from the guanylyltransferase, and yet others may encode a novel class of RNA triphosphatase. Nonetheless, a survey of current unicellular genome databases suggests that other protozoans (including Dictyostelium and the pathogenic parasite Trypanosoma) do indeed have ORFs encoding polypeptides that resemble fungal RNA triphosphatases. Thus, antimalarial inhibitors of Plasmodium RNA triphosphatase may be effective against a battery of other unicellular parasites that cause human disease.

Therefore, the present invention provides an isolated DNA encoding a mRNA capping enzyme GTP:RNA guanylyltransferase of *Plasmodium falciparum*, wherein the amino acid sequence of said enzyme is shown in SEQ ID No. 1. The present invention also provides a recombinant expression vector comprising this DNA, or a fragment thereof that encodes active guanylyltransferase, wherein said DNA is operably linked to regulatory elements that control the expression of said DNA in a host cell. The present invention also provides a host cell transformed with this vector and an isolated polypeptide, or a fragment thereof that possesses guanylyltransferase activity. wherein said polypeptide is encoded by this DNA or a mutated version of this DNA.

In addition, the present invention is directed to a method of screening for a compound that inhibits the catalytic activity of Plasmodium guanylyltransferase, comprising the steps of:
contacting said guanylyltransferase with a guanosine triphosphate substrate and a divalent cation cofactor in the presence or absence of said compound; and detecting formation of a covalent guanylyltransferase-GMP intermediate, wherein a lack of formation of said intermediate or a decrease in formation of said intermediate indicates said compound inhibits the catalytic activity of said guanylyltransferase. Preferably, the divalent cation cofactor is selected from the group consisting of manganese and magnesium and the guanosine triphosphate substrate is selected from the group consisting of radioisotopically-labeled guanosine triphosphate and fluorescence-labeled guanosine triphosphate analogs. Generally, the detection of covalent intermediate formation is by a method selected from the group consisting of radioisotope assay and fluorescence assay. The detection of covalent intermediate formation may be by a method selected from the group consisting of analyzing the reaction products by polyacrylamide gel electrophoresis and applying the reaction products to a filter or other solid support so as to retain the guanylyltransferase-GMP intermediate on said filter or solid support without retaining the GTP substrate or pyrophosphate product. Preferably, the Plasmodium guanylyltransferase has the amino acid sequence of SEQ ID No. 1, is a fragment of the guanylyltransferase with the amino acid sequence of SEQ ID No. 1, or is a mutated version of the guanylyltransferase with the amino acid sequence of SEQ ID No. 1. The compound is selected from the group consisting of chemicals, drugs and proteins.

In addition, the present invention is directed to a method of screening for a compound that inhibits the catalytic activity of Plasmodium guanylyltransferase, comprising the steps of:
contacting said Plasmodium guanylyltransferase with a guanosine triphosphate substrate and a divalent cation cofactor and a diphosphate-terminated RNA in the presence or absence of said compound; and detecting formation of a GMP-capped RNA, wherein a lack of formation of said GMP-capped RNA or a decrease in formation of said GMP-capped RNA indicates said compound inhibits the catalytic activity of said guanylyltransferase. The Plasmodium guanylyltransferase may have the amino acid sequence of SEQ ID No. 1, is a fragment of the guanylyltransferase with the amino acid sequence of SEQ ID No. 1, or is a mutated version of the guanylyltransferase with the amino acid sequence of SEQ ID No. 1.

In addition, the present invention is directed to an isolated DNA encoding a mRNA capping enzyme RNA 5' triphosphatase of *Plasmodium falciparum*, wherein the amino acid sequence of said enzyme is shown in SEQ ID No. 2. A recombinant expression vector comprising this DNA or a fragment thereof that encodes active RNA 5' triphosphatase, wherein said DNA is operably linked to regulatory elements that control the expression of said DNA in a host cell is also provided as is a host cell transformed with this vector.

In addition, the present invention is directed to an isolated polypeptide, or a fragment thereof that possesses RNA 5' triphosphatase activity, wherein said polypeptide is encoded by the DNA of the present invention or a mutated version thereof.

In addition, the present invention is directed to a method of screening for a compound that inhibits the catalytic activity of the RNA 5' triphosphatase component of the mRNA capping apparatus of a unicellular eukaryotic parasite, comprising the steps of: contacting said unicellular parasite-encoded RNA 5' triphosphatase with a nucleoside triphosphate substrate and a divalent cation cofactor in the presence or absence of said compound; and detecting hydrolysis of said nucleoside triphosphate to a nucleoside diphosphate and inorganic phosphate, wherein a lack of hydrolysis of said nucleoside triphosphate or a decrease in hydrolysis of said nucleoside triphosphate indicates said compound inhibits the catalytic activity of said parasite-encoded triphosphatase. The unicellular eukaryotic parasite may be, e.g., Plasmodia, Trypanosoma, Leishmania, Toxoplasma, Cryptosporidia, Giardia, Entamoeba, Trichomonas, and Microsporidia. Representative Plasmodium parasits include *Plasmodium falciparum, Plasmodium vivax, Plasmodium ovale*, and *Plasmodium malariae*. The parasite-encoded RNA 5' triphosphatase may have the amino acid sequence of SEQ ID No. 2, is a fragment of the triphosphatase with the amino acid sequence of SEQ ID No. 2, or is a mutated version of the triphosphatase with the amino acid sequence of SEQ ID No. 2.

Furthermore, the present invention is directed to a method of screening for a compound that inhibits the catalytic activity of the RNA 5' triphosphatase component of the mRNA capping apparatus of a unicellular eukaryotic parasite, comprising the steps of: contacting said unicellular parasite-encoded triphosphatase with a 5' triphosphate RNA substrate and a divalent cation cofactor in the presence or absence of said compound; and detecting hydrolysis of said triphosphate RNA to a diphosphate RNA and inorganic phosphate, wherein a lack of hydrolysis of said triphosphate RNA or a decrease in hydrolysis of said triphosphate RNA indicates said compound inhibits the catalytic activity of said parasite-encoded triphosphatase.

The following references were cited herein:
1. Newton and White (1999) Ann. Rev. Med. 5 0, 179–192.
2. Gardner (1999) Curr. Opin. Genet. Dev. 9, 704–708.
3. Shuman (2000) Prog. Nucleic Acid Res. Mol. Biol. 66, 1–40.

4. Ho and Shuman (2001) J. Virol. (in press).
5. Lima et al. (1999) Cell 99, 533–543.
6. Ho et al. (1998) J. Biol. Chem. 273, 34151–34156.
7. Yu et al. (1997) J. Virol. 71, 9837–9843.
8. Silva et al. (1998) Mol. Cell. Biol. 18, 4612–4619.
9. Håkansson et al. (1997) Cell 89, 545–553.
10. Wang et al. (1997) Proc. Natl. Acad. Sci. USA 94, 9573–9578.
11. Gross and Shuman (1998) J. Virol. 72, 10020–10028.
12. Pei et al. (1999) J. Biol. Chem. 274, 28865–28874.
13. Pei et al. (2000) Nucleic Acids Res. 28, 1885–1892.
14. Pei et al. (2001) Nucleic Acids Res. (in press).
15. Ho et al. (1998) J. Biol. Chem. 273, 9577–9585.
16. Martins and Shuman (2000) J. Biol. Chem. 275, 35070–35076.
17. Deshpande et al. (1999). J. Biol. Chem. 274, 16590–4.
18. Altschul et al. (1997) Nucleic Acids Res. 25, 3389–3402.
19. Lanzetta et al. (1979) Anal. Biochem. 100, 95–97.
20. Webb (1992) Proc. Natl. Acad. Sci. USA 89, 4884–4887.
21. Brune et al. (1994) Biochemistry 33, 8262–8271.
22. Brune et al. (1998) Biochemistry 37, 10370–10380.
23. Baldauf et al. (2000) Science 290, 972–977.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for a compound that inhibits the catalytic activity of *Plasmodium guanylyltransferase*, comprising the steps of:

contacting said *Plasmodium guanylyltransferase* of SEQ ID NO: 1 or an enzymatically active fragment thereof with a guanosine triphosphate substrate and a divalent cation cofactor and a diphosphate-terminated RNA in the presence or absence of said compound; and detecting formation of a GMP-capped RNA, wherein a lack of formation of said GMP-capped RNA or a decrease in formation of said GMP-capped RNA indicates said compound inhibits the catalytic activity of said guanylyltransferase.

2. The method of claim 1, wherein said divalent cation cofactor is selected from the group consisting of manganese and magnesium.

3. The method of claim 1, wherein said guanosine triphosphate substrate is selected from the group consisting of radioisotopically-labeled guanosine triphosphate and fluorescence-labeled guanosine triphosphate analogs.

4. The method of claim 1, wherein said detection of GMP-capped RNA formation is by a method selected from the group consisting of a radioisotope assay and a fluorescence assay.

5. The method of claim 1, wherein said detection of GMP-capped RNA formation is by a method selected from the group consisting or analyzing the reaction products by polyacrylamide gel electrophoresis and applying the reaction products to a filter or other solid support so as to retain the GMP-capped RNA on said filter or solid support without retaining the GTP substrate or pyrophosphate product.

6. The method of claim 1, wherein said *Plasmodium guanylyltransferase* has the amino acid sequence of SEQ ID No. 1.

7. The method of claim 1, wherein said compound is selected from the group consisting of chemicals, drugs and proteins.

* * * * *